(12) United States Patent
Atwell et al.

(10) Patent No.: US 7,026,446 B1
(45) Date of Patent: Apr. 11, 2006

(54) BIFUNCTIONAL MOLECULES

(75) Inventors: John Leslie Atwell, Vermont South (AU); Peter Leonard Devine, Cairndale (AU); Gregory Coia, Brunswick (AU); Alexander Andrew Kortt, Strathmore (AU); Gillian Wendy Perry, Werribee (AU); Peter Gregory Bundesen, Fig Tree Pocket (AU)

(73) Assignee: Diatech Pty Ltd. (AU)

( * ) Notice: Subject to any disclaimer, the term of this patent is extended or adjusted under 35 U.S.C. 154(b) by 0 days.

(21) Appl. No.: 09/581,924

(22) PCT Filed: Dec. 24, 1998

(86) PCT No.: PCT/AU98/01076

§ 371 (c)(1),
(2), (4) Date: Jun. 19, 2000

(87) PCT Pub. No.: WO99/33965

PCT Pub. Date: Jul. 8, 1999

(30) Foreign Application Priority Data

Dec. 24, 1997 (AU) .............................................. PP1110
Aug. 11, 1998 (AU) .............................................. PP5176

(51) Int. Cl.
*C07K 16/46* (2006.01)
*C07K 14/31* (2006.01)
*C07K 14/315* (2006.01)
*C07K 14/435* (2006.01)
*C07K 14/705* (2006.01)

(52) U.S. Cl. ................. 530/350; 530/387.1; 530/387.2; 530/387.3; 530/388.1; 530/388.15; 530/388.22; 530/412

(58) Field of Classification Search .............. 530/387.1, 530/387.2, 387.3, 388.1, 388.15, 388.22, 530/412, 350
See application file for complete search history.

(56) References Cited

U.S. PATENT DOCUMENTS

| | | | | |
|---|---|---|---|---|
| 4,681,782 A | * | 7/1987 | Ozkan | 428/35.7 |
| 4,876,194 A | * | 10/1989 | Bjorck et al. | 435/68.1 |
| 5,096,670 A | * | 3/1992 | Harris et al. | 422/65 |
| 5,560,911 A | * | 10/1996 | Koren et al. | |
| 5,583,202 A | * | 12/1996 | Zanetti | |
| 5,620,889 A | * | 4/1997 | Lynch et al. | 435/332 |
| 5,665,558 A | * | 9/1997 | Frame et al. | 435/7.25 |
| 5,723,125 A | * | 3/1998 | Chang et al. | 424/134.1 |
| 6,057,421 A | * | 5/2000 | Muller et al. | |
| 6,207,815 B1 | * | 3/2001 | Mezes et al. | |

FOREIGN PATENT DOCUMENTS

| | | |
|---|---|---|
| EP | 0 617 127 | 9/1994 |
| JP | 02 264863 | 10/1990 |
| WO | WO 91/13166 * | 9/1991 |
| WO | WO 97/27486 | 7/1997 |

OTHER PUBLICATIONS

Translation of JP 64060388.*
The abstract of Borza et al (Biochemistry, 1996, vol. 35, pp. 1925–1934).*
The abstract of Gorgani et al (Biochemistry, 1997, vol. 36, pp. 6653–6662).*
The abstract of Sekisui–Chem (Database Biotechds, Thomson Derwent, ISI on STN, Accession No. 1990–01279, JP 01060388, Mar. 7, 1989.*
Zeltzer and Seeger (Journal of Immunological Methods, 1977, vol. 17, pp. 163–175).*
Paul (Fundamental Immunology (text), 1993, pp. 296–302.*
Gillies et al, Humn antibodies and Hybridomas, 1990, vol. 1, pp. 47–54, (abstract).*
Mueller et al, PNAS, 1990, vol. 87, pp. 5702–5705. (abstract).*
Artandi et al, Journal of Immunology, 1991, vol. 146, pp. 603–610.*
Mogan, WT, "Human serum histidine rich glycoprotein", Biochim Biophys Acta, 1978, vol. 535, pp. 319–333.*
Lijnen et al, "Physiochemical, immunochemical and functional comparison of human histidine rich glycoprotein and autorosette inhibition factor", Biochim Biophys Acta, 1983, vol. 742, pp. 109–115.*
Angles–Carno et al, "Plasminogen binding by alpha2–antiplasmin and hisidine rich glycoprotein" Biochim Biophys Acta, 1992, vol. 1156, pp. 34–42.*
Paul, Fundamental Immunology (textbook), 1993, 3rd edition, p. 250–251.*
Yamamoto et al, "Anti–idiotype monoclonal antibody carrying the internal image of ganglioside GM3", J of the National Cancer Institute, 1990, vol. 82, pp. 1757–1760.*

(Continued)

*Primary Examiner*—Karen A. Canella
(74) *Attorney, Agent, or Firm*—Frommer Lawrence & Haug; Thomas J. Kowalski

(57) ABSTRACT

The invention relates to a chimeric antibody conjugate comprising an antigen binding region of a non-human antibody and an immunoglobulin constant region which comprises at least one $C_H$ domain or epitope thereof, with the proviso that the constant region is not a naturally occurring $F_C$ fragment. A bifunctional molecule for use in labelling an antibody derived from a first species, the bifunctional molecule comprising a binding region which binds to the antibody of the first species or to one or more groups provided thereon, and a constant region derived from an antibody of a second species, the constant region comprising at least one $C_H$ domain or an epitope thereof. The present invention relates to bifunctional molecules and complexes which are useful as positive control reagents in antibody based diagnostic tests. The present invention also relates to polynucleotides encoding these bifunctional molecules, and to diagnostic assays involving the use of these molecules.

17 Claims, 11 Drawing Sheets

OTHER PUBLICATIONS

Kronvall and Williams, "Differences in anti–protein A activity among IgF subgroups", J of Immunology, 1969, vol. 103, pp. 828–833.*

Bjorck and Kronvall, "Purification and some properties of streptococcal protein G" J of Immunology, 1984, vol. 133, pp. 969–974.*

Atkinson et al, "Cloning, expression and purification of Ppl–1, a kappa–chain binding protein" Bioseparation, 1995, vol. 5, pp. 359–367.*

Better et al, "T–cell targeted immunofusion proteins from *Escherichia coli*", Journal of Biological Chemistry, vol. 270, pp. 14951–14957, Jun. 1995.*

Borrebaeck, C.A.K. (ed)., Antibody Engineering ($2^{nd}$ ed.), Oxford University Press, Inc. pp. 205–255, 1995.

Spooner et al., Human Pathology, vol. 25, No. 6, pp. 606–614, Jun. 1994.

Wright et al., Critical Reviews in Immunology, vol. 12, Nos. 3 & 4, pp. 125–168, 1992.

Pearce et al., Biochemistry and Biology International, vol. 42, No. 6, 1179–1188, Sep. 1997.

Coloma et al., Nature Biotechnology, vol. 15, pp. 159–163, Feb. 1997.

Yanamura et al., Jpn. J. Cancer Res., vol. 187, pp. 405–411, Apr. 1996.

Flamez et al., Journal of Biotechnology, vol. 42, pp. 133–143, 1995.

Sandhu et al., Critical Reviews in Biotechnology, vol. 12, Nos 5 & 6, pp. 437–462, 1992.

Calvo etal., Cancer Biotherapy, vol. 8, No. 1, pp. 95–109, 1993.

Jin et al., Molecular Immunology, vol. 130, No. 18, pp. 1647–1654, 1993.

* cited by examiner

Region 1          Region 2
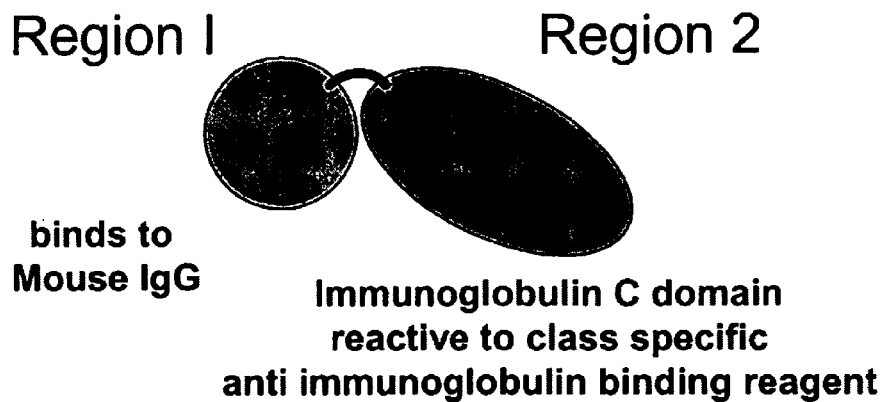
binds to Mouse IgG
Immunoglobulin C domain reactive to class specific anti immunoglobulin binding reagent
Complex formed between bifunctional molecule and mouse IgG
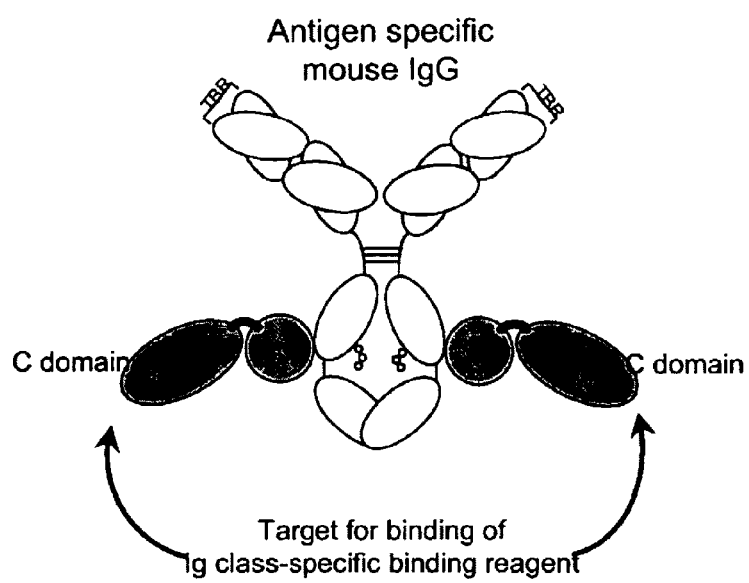
Antigen specific mouse IgG
C domain          C domain
Target for binding of Ig class-specific binding reagent
FIG. 3

```
              M   K   Y   L   L   P   T   A   A   A   G   L   L   L   L   A
2353         ATG AAA TAC CTA TTG CCT ACG GCA GCC GCT GGA TTG TTA TTA CTC GCG
             \-- Pel B-- -->                                                 -
              A   Q   P   A   M   A   A   D   N   K   F   N   K   E   Q   Q
2401         GCC CAG CCG GCC ATG GCC GCG GAT AAC AAA TTC AAC AAA GAA CAA CAA
             --- Sfi 1    <N col >   < Start Fragment B
              N   A   F   Y   E   I   L   H   L   P   N   L   N   E   E   Q
2449         AAT GCT TTC TAT GAA ATC TTA CAT TTA CCT AAC TTA AAC GAA GAA CAA R   N   G   F   I   Q   S   L   K   D   D   P   S   Q   S   A
2497         CGC AAT GGT TTC ATC CAA AGC CTA AAA GAT GAC CCA AGC CAA AGC GCT N   L   L   A   E   A   K   K   L   N   D   A   Q   A   P   K
2545         AAC CTT TTA GCA GAA GCT AAA AAG CTA AAT GAT GCT CAA GCA CCA AAA
                                                                 End Fragment B->
              S   D   P   A   A   A   D   Q   D   T   A   I   R   V   F   A
2593         AGT GAT CCC GCG GCC GCA GAT CAA GAC ACA GCC ATC CGG GTC TTC GCC
             < linker >     Not1   >   CH3 mu domain
              I   P   P   S   F   A   S   I   F   L   T   K   S   T   K   L
2641         ATC CCC CCA TCC TTT GCC AGC ATC TTC CTC ACC AAG TCC ACC AAG TTG T   C   L   V   T   D   L   T   T   Y   D   S   V   T   I   S
2689         ACC TGC CTG GTC ACA GAC CTG ACC ACC TAT GAC AGC GTG ACC ATC TCC W   T   R   Q   N   G   E   A   V   K   T   H   T   N   I   S
2737         TGG ACC CGC CAG AAT GGC GAA GCT GTG AAA ACC CAC ACC AAC ATC TCC E   S   H   P   N   A   T   F   S   A   V   G   E   A   S   I
2785         GAG AGC CAC CCC AAT GCC ACT TTC AGC GCC GTG GGT GAG GCC AGC ATC C   E   D   D   W   N   S   G   E   R   F   T   C   T   V   T
2833         TGC GAG GAT GAC TGG AAC TCC GGG GAG AGG TTC ACG TGC ACC GTG ACC H   T   D   L   P   S   P   L   K   Q   T   I   S   R   P   K
2881         CAC ACA GAC CTG CCC TCG CCA CTG AAG CAG ACC ATC TCC CGG CCC AAG G   A   A   D   Y   K   D   D   D   D   K   *
2929         GGc GCC GCG GAT TAT AAA GAT GAT GAT GAT AAA TAA GAA TTC AGC CCG
             Sac 2       ------------ FLAG -------------      Eco R1  <-------

2977         CCT AAT GAG CGG GCT TTT TTT TAA TTC ACT GGC CGT CGT TTT ACA ACG
             -------- TrpA terminator ----->
```

FIG. 8

Sequence of expression cassette Str-C$_H$3μ in pGC vector

```
         M   K   Y   L   L   P   T   A   A   A   G   L   L   L   L   A
2353    ATG AAA TAC CTA TTG CCT ACG GCA GCC GCT GGA TTG TTA TTA CTC GCG
        \-- Pel B-- -->                                                 -
         A   Q   P   A   M   A   E   A   G   I   T   G   T   W   Y   N
2401    GCC CAG CCG GCC ATG GCC gag gcc ggc atc acc ggc acc tgg tac aac
        --- Sfi 1    <N co1 >-- -corestreptavidin ---------------->
         Q   L   G   S   T   F   I   V   T   A   G   A   D   G   A   L
2449    cag ctc ggc tcg acc ttc atc gtg acc gcg ggc gcc gac ggc gcc ctg T   G   T   Y   E   S   A   V   G   N   A   E   S   R   Y   V
2497    acc gga acc tac gag tcg gcc gtc ggc aac gcc gag agc cgc tac gtc L   T   G   R   Y   D   S   A   P   A   T   D   G   S   G   T
2545    ctg acc ggt cgt tac gac agc gcc ccg gcc acc gac ggc agc ggc acc A   L   G   W   T   V   A   W   K   N   N   Y   R   N   A   H
2593    gcc ctc ggt tgg acg gtg gcc tgg aag aat aac tac cgc aac gcc cac S   A   T   T   W   S   G   Q   Y   V   G   G   A   E   A   R
2641    tcc gcg acc acg tgg agc ggc cag tac gtc ggc ggc gcc gag gcg agg I   N   T   Q   W   L   L   T   S   G   T   T   E   A   N   A
2689    atc aac acc cag tgg ctg ctg acc tcc ggc acc acc gag gcc aac gcc W   K   S   T   L   V   G   H   D   T   F   T   K   V   K   P
2737    tgg aag tcc acg ctg gtc ggc cac gac acc ttc acc aag gtg aag ccg
                                                            |-end core
         S   A   A   S   D   P   A   A   A   D   Q   D   T   A   I   R
2785    tcc gcc gct agc gat ccc gcg gcc gca gat caa gac aca gcc atc cgg
        strep-|  -   <l ink er>  <-N ot1  >  CH3 mu
         V   F   A   I   P   P   S   F   A   S   I   F   L   T   K   S
2833    gtc ttc gcc atc ccc cca tcc ttt gcc agc atc ttc ctc acc aag tcc T   K   L   T   C   L   V   T   D   L   T   T   Y   D   S   V
2881    acc aag ttg acc tgc ctg gtc aca gac ctg acc acc tat gac agc gtg
         T   I   S   W   T   R   Q   N   G   E   A   V   K   T   H   T
2929    acc atc tcc tgg acc cgc cag aat ggc gaa gct gtg aaa acc cac acc N   I   S   E   S   H   P   N   A   T   F   S   A   V   G   E
2977    aac atc tcc gag agc cac ccc aat gcc act ttc agc gcc gtg ggt gag A   S   I   C   E   D   D   W   N   S   G   E   R   F   T   C
3025    gcc agc atc tgc gag gat gac tgg aac tcc ggg gag agg ttc acg tgc T   V   T   H   T   D   L   P   S   P   L   K   Q   T   I   S
3073    acc gtg acc cac aca gac ctg ccc tcg cca ctg aag cag acc atc tcc R   P   K   G   A   A   D   Y   K   D   D   D   D   K   *
3121    cgg ccc aag ggc gcc gcg gat tat aaa gat gat gat gat aaa taa GAA
                                Sac 2   --- --- --- -FL AG --- --- ---   Eco
```

FIG. 10

SEQUENCE LISTING

```
<160> NUMBER OF SEQ ID NOS: 4

<210> SEQ ID NO 1
<211> LENGTH: 203
<212> TYPE: PRT
<213> ORGANISM: Artificial Sequence
<220> FEATURE:
<223> OTHER INFORMATION: Description of Artificial Sequence: Artificial
      sequence comprising sequence from Staphylococcal protein A fused
      to a sequence from human immunoglobulin

<400> SEQUENCE: 1

Met Lys Tyr Leu Leu Pro Thr Ala Ala Ala Gly Leu Leu Leu Leu Ala
1               5                   10                  15

Ala Gln Pro Ala Met Ala Ala Asp Asn Lys Phe Asn Lys Glu Gln Gln
            20                  25                  30

Asn Ala Phe Tyr Glu Ile Leu His Leu Pro Asn Leu Asn Glu Glu Gln
        35                  40                  45

Arg Asn Gly Phe Ile Gln Ser Leu Lys Asp Asp Pro Ser Gln Ser Ala
    50                  55                  60

Asn Leu Leu Ala Glu Ala Lys Lys Leu Asn Asp Ala Gln Ala Pro Lys
65                  70                  75                  80

Ser Asp Pro Ala Ala Ala Asp Gln Asp Thr Ala Ile Arg Val Phe Ala
                85                  90                  95

Ile Pro Pro Ser Phe Ala Ser Ile Phe Leu Thr Lys Ser Thr Lys Leu
            100                 105                 110

Thr Cys Leu Val Thr Asp Leu Thr Thr Tyr Asp Ser Val Thr Ile Ser
        115                 120                 125

Trp Thr Arg Gln Asn Gly Glu Ala Val Lys Thr His Thr Asn Ile Ser
    130                 135                 140

Glu Ser His Pro Asn Ala Thr Phe Ser Ala Val Gly Glu Ala Ser Ile
145                 150                 155                 160
```

```
Cys Glu Asp Asp Trp Asn Ser Gly Glu Arg Phe Thr Cys Thr Val Thr
                165                 170                 175

His Thr Asp Leu Pro Ser Pro Leu Lys Gln Thr Ile Ser Arg Pro Lys
            180                 185                 190

Gly Ala Ala Asp Tyr Lys Asp Asp Asp Lys
        195                 200
```

<210> SEQ ID NO 2
<211> LENGTH: 672
<212> TYPE: DNA
<213> ORGANISM: Artificial Sequence
<220> FEATURE:
<223> OTHER INFORMATION: Description of Artificial Sequence: Artificial
      sequence comprising sequence from Staphylococcal protein A fused
      to a sequence from human immunoglobulin

<400> SEQUENCE: 2

```
atgaaatacc tattgcctac ggcagccgct ggattgttat tactcgcggc ccagccggcc     60
atggccgcgg ataacaaatt caacaaagaa caacaaaatg ctttctatga aatcttacat    120
ttacctaact aaacgaaga caacgcaat ggtttcatcc aaagcctaaa agatgaccca      180
agccaaagcg ctaaccttt agcagaagct aaaaagctaa atgatgctca agcaccaaaa     240
agtgatcccg cggccgcaga tcaagacaca gccatccggg tcttcgccat ccccccatcc    300
tttgccagca tcttcctcac caagtccacc aagttgacct gcctggtcac agacctgacc    360
acctatgaca gcgtgaccat ctcctggacc cgccagaatg cgaagctgt gaaaacccac     420 accaacatct ccgagagcca ccccaatgcc actttcagcg ccgtgggtga ggccagcatc    480
tgcgaggatg actggaactc cggggagagg ttcacgtgca ccgtgaccca cacagacctg    540
ccctcgccac tgaagcagac catctcccgg cccaagggcg ccgcggatta taaagatgat    600
gatgataaat aagaattcag cccgcctaat gagcgggctt ttttttaatt cactggccgt    660
cgttttacaa cg                                                       672
```

<210> SEQ ID NO 3
<211> LENGTH: 270
<212> TYPE: PRT
<213> ORGANISM: Artificial Sequence
<220> FEATURE:
<223> OTHER INFORMATION: Description of Artificial Sequence: Artificial
      sequence comprising sequence from S. avidini fused to a sequence
      from human immunoglobulin

<400> SEQUENCE: 3

```
Met Lys Tyr Leu Leu Pro Thr Ala Ala Ala Gly Leu Leu Leu Leu Ala
  1               5                  10                  15

Ala Gln Pro Ala Met Ala Glu Ala Gly Ile Thr Gly Thr Trp Tyr Asn
             20                  25                  30

Gln Leu Gly Ser Thr Phe Ile Val Thr Ala Gly Ala Asp Gly Ala Leu
         35                  40                  45

Thr Gly Thr Tyr Glu Ser Ala Val Gly Asn Ala Glu Ser Arg Tyr Val
     50                  55                  60

Leu Thr Gly Arg Tyr Asp Ser Ala Pro Ala Thr Asp Gly Ser Gly Thr
 65                  70                  75                  80

Ala Leu Gly Trp Thr Val Ala Trp Lys Asn Asn Tyr Arg Asn Ala His
                 85                  90                  95

Ser Ala Thr Thr Trp Ser Gly Gln Tyr Val Gly Gly Ala Glu Ala Arg
            100                 105                 110
```

-continued

```
Ile Asn Thr Gln Trp Leu Leu Thr Ser Gly Thr Thr Glu Ala Asn Ala
        115                 120                 125

Trp Lys Ser Thr Leu Val Gly His Asp Thr Phe Thr Lys Val Lys Pro
    130                 135                 140

Ser Ala Ala Ser Asp Pro Ala Ala Asp Gln Asp Thr Ala Ile Arg
145                 150                 155                 160

Val Phe Ala Ile Pro Pro Ser Phe Ala Ser Ile Phe Leu Thr Lys Ser
                165                 170                 175

Thr Lys Leu Thr Cys Leu Val Thr Asp Leu Thr Thr Tyr Asp Ser Val
                180                 185                 190

Thr Ile Ser Trp Thr Arg Gln Asn Gly Glu Ala Val Lys Thr His Thr
        195                 200                 205

Asn Ile Ser Glu Ser His Pro Asn Ala Thr Phe Ser Ala Val Gly Glu
    210                 215                 220

Ala Ser Ile Cys Glu Asp Asp Trp Asn Ser Gly Glu Arg Phe Thr Cys
225                 230                 235                 240

Thr Val Thr His Thr Asp Leu Pro Ser Pro Leu Lys Gln Thr Ile Ser
                245                 250                 255

Arg Pro Lys Gly Ala Ala Asp Tyr Lys Asp Asp Asp Lys
                260                 265                 270
```

<210> SEQ ID NO 4
<211> LENGTH: 864
<212> TYPE: DNA
<213> ORGANISM: Artificial Sequence
<220> FEATURE:
<223> OTHER INFORMATION: Description of Artificial Sequence: Artificial
      sequence comprising sequence from S. avidini fused to a sequence
      from human immunoglobulin

<400> SEQUENCE: 4

```
atgaaatacc tattgcctac ggcagccgct ggattgttat tactcgcggc ccagccggcc      60
atggccgagg ccggcatcac cggcacctgg tacaaccagc tcggctcgac cttcatcgtg     120
accgcgggcg ccgacggcgc cctgaccgga acctacgagt cggccgtcgg caacgccgag     180
agccgctacg tcctgaccgg tcgttacgac agcgccccgg ccaccgacgg cagcggcacc     240
gccctcggtt ggacggtggc ctggaagaat aactaccgca acgcccactc cgcgaccacg     300
tggagcggcc agtacgtcgg cggcgccgag gcgaggatca cacccagtg gctgctgacc      360
tccggcacca ccgaggccaa cgcctggaag tccacgctgg tcggccacga cccttcacc      420
aaggtgaagc cgtccgccgc tagcgatccc gcggccgcag atcaagacac agccatccgg     480
gtcttcgcca tcccccccatc ctttgccagc atcttcctca ccaagtccac caagttgacc    540
tgcctggtca cagacctgac cacctatgac agcgtgacca tctcctggac ccgccagaat     600
ggcgaagctg tgaaaaccca caccaacatc tccgagagcc accccaatgc cactttcagc     660
gccgtgggtg aggccagcat ctgcgaggat gactggaact ccggggagag gttcacgtgc     720
accgtgaccc acacagacct gccctcgcca ctgaagcaga ccatctcccg gcccaagggc     780
gccgcggatt ataagatga tgatgataaa taagaattca gcccgcctaa tgagcgggct     840
ttttttttaat tcactggccg tcgt                                            864
```

BIFUNCTIONAL MOLECULES

This application is the National Phase of PCT/AU98/01076, filed Dec. 24, 1998, designating the U.S. and published as WO 99/33965, with claims of priority from Australian application Nos. PP 1110 and PP5176, filed Dec. 24, 1997 and Aug. 11, 1998. All of the foregoing applications, as well as all documents cited in the foregoing applications ("application documents") and all documents cited or referenced in application documents are hereby incorporated herein by reference. Also, all documents cited in this application ("herein cited documents") and all documents cited or referenced in herein cited documents are hereby incorporated herein by reference.

FIELD OF THE INVENTION

The present invention relates to bifunctional molecules and complexes which are useful as a positive control reagents in antibody based diagnostic tests. The present invention also relates to polynucleotides encoding these bifunctional molecules, and to diagnostic assays involving the use of these molecules.

BACKGROUND OF THE INVENTION

Infection of humans by any micro-organisms leads to the initiation of a humoral immune response that can be used in the diagnosis of the disease. In the early acute phase of the infection, specific IgM class antibodies are the first to appear in serum 1–4 weeks after the onset of symptoms and last for up to three months. IgG class antibodies appear later and remain elevated throughout the patient's life. Detection of an IgM response is indicative of a recent or current infection, while the presence of an elevated IgG response is a marker for past exposure to the causative agent. Specific IgM or IgG responses to a particular infectious agent can be measured by antibody based diagnostic tests such as ELISA, immunochromatography, particle agglutination ELISA, biosensor or other similar assays.

These assays require the use of reactive human sera as a positive control. The positive control reagent is usually serum taken from a patient or animal which is known to have a positive reaction to the particular antigen under test. If the test is designed to distinguish between early and late infection (via the differentiation between immunoreactive IgM, for early infection and IgG, for late or previous infection), the positive control serum or reagent should contain immunoreactive antibody of the correct immunoglobulin class.

It is becoming increasingly difficult to source sufficient quantities of immune human sera or plasma, particularly as diagnostic tests for rarer diseases become available. Collection of blood for IgM controls from patients in early stages of infection when clinical symptoms are generally most severe poses significant ethical problems, particularly if the disease primarily affects juveniles. Other drawbacks include the requirement for consistent collections from remote locations, the need to standardise each batch and to check for contamination with infectious agents such as HIV, hepatitis B and hepatitis C. There are also problems in obtaining control sera for specific endemic diseases in communities where the donation of blood or blood products is socially unacceptable.

There is therefore a need for a source of positive control reagents which does not rely on being obtained from human donors.

Hybridoma technology provides a plentiful supply of monoclonal antibodies, but as these are generally of murine origin, they do react with binding reagents used to quantify human antibodies. Intact functional mouse/human chimeric antibodies have been described in the literature for some time (Boulianne et al., 1984, Morrison et al., 1984; Winter et al., 1991). In these constructs the antigen binding function residing in a mouse Fab or Fv fragment has been grafted on to a human Ig backbone and expressed in hybridoma cells. In some cases these reshaped molecules have been designed for human therapy, utilising the effector functions of the human Fc for targeting (Reichmann et al., 1988). Others have been designed as positive control reagent substitutes (Hamilton, 1990, 1991), where $V_H$ and $V_L$ regions from a mouse monoclonal antibody of desired specificity have been grafted onto either a human IgG or IgM backbone.

Synthetic positive control reagents are available from a limited number of sources. U.S. Pat. No. 4,929,543 relates to chimeric antibody fragments where Fab or F(ab')2 fragments of non human origin, with specificity for the desired antigen, are chemically coupled to human Fc fragments in order to confer upon the reactive non-human Fab fragments epitopes recognised by class specific anti human immunoglobulin antisera. This reference does not teach or suggest coupling non-human Fab or F(ab')2 fragments to individual $C_H$ domains in order to provide epitopes for recognition by class specific anti human immunoglobulin antisera. Furthermore, production of the chimeric fragments is entirely by synthetic routes based upon digestion of antibodies, purification of fragments and chemical linking to create the chimera.

Labor Diagnostika GmbH of Heiden, Germany have produced synthetic positive control reagents which are formed by chemical attachments of non human Fab fragments and human Fc fragments onto a latex bead. These attachments confer upon the bead the twin properties required of a positive control reagent—specific antigen binding and human immunoglobulin class specific epitopes.

A process for producing positive control reagents which circumvents the requirement to manipulate full length Fc fragments or to manipulate VH and VL sequences for each new control reagent specificity is desirable.

SUMMARY OF THE INVENTION

The present inventors have now developed bifunctional molecules which may be used as positive control reagents in antibody based diagnostic tests.

In one aspect of the present invention, the bifunctional molecule is a chimeric antibody conjugate comprising a first region which binds a specific antigen and a second region comprising at least one constant domain sequence derived from a class specific immunoglobulin. This conjugate, which may be used directly as a positive control reagent, avoids the inconvenience of manipulating full length or naturally occurring Fc fragments. Furthermore, the conjugate may be readily produced by recombinant DNA technology.

Accordingly, in a first aspect the present invention provides a chimeric antibody conjugate comprising an antigen binding region derived from a non-human antibody and a constant region which comprises at least one $C_H$ domain or epitope thereof, with the proviso that the constant region is not a naturally occurring $F_C$ fragment.

When used herein, "naturally occurring Fc fragment" means a full length naturally occurring Fc fragment which may be derived by proteolytic digestion of an intact antibody molecule. For example, a naturally occurring Fc fragment of IgM will comprise domains $C_H2$, $C_H3$ and $C_H4$, whereas a naturally occurring IgG Fc fragment will comprise $C_H2$ and $C_H3$ domains.

By "chimeric" we mean that the constant region is derived from a different species than the antigen binding region.

In a preferred embodiment the non-human antigen binding region comprises or consists of a non-human Fab fragment or part thereof. The non-human antigen binding region may comprise or consist of an scFv fragment.

In a further preferred embodiment the non-human antigen binding region is derived from a mouse.

In a preferred embodiment the constant region is derived from a human antibody. It will be appreciated, however, that the constant region may be a non-human (such as bovine, canine, ovine, equine, feline or caprine) constant region in cases where the chimeric construct is to be used as a positive antibody control in assays involving sera derived from non-human species.

The constant region may consist of a non-naturally occurring combination of $C_H$ domains or epitopes thereof. The constant region may consist of two $C_H$ domains of the same type, for example, two $C_H3$ domains. Alternatively, the constant region may consist of two different domains. The two different domains, or epitopes, thereof may be derived from antibodies of different classes. In a preferred embodiment, the constant region consists of a single $C_H$ domain.

In a particularly preferred embodiment of the present invention the chimeric antibody conjugate is suitable as a positive IgM control and the constant region comprises one or more $C_H3\mu$ domains.

In a further preferred embodiment the non-human antigen binding region binds to an epitope derived from an infectious agent selected from but not limited to dengue virus, rubella virus, herpes virus, parvovirus, human glycophorin, *Rickettsia sibirica*, *Burkholeria pseudomallei*, *Salmonella typhi* or *paratyphi*, *Leptospira interrogans*, *Plasmodium falciparum/vivax*, Japanese encephalitis virus, Yellow fever virus, *Bordetella pertussis/parapertussis*, *Candida albicans/kruzei*, *Varicella zoster* virus, HIV, Hepatitis viruses, Human papilloma virus, Epstein-Barr virus, Ross River virus, *Brucella abortis*, Human herpesvirus-6, Parvovirus B19, *Coxiella burnettii*, Herpes simplex viruses 1&2, *Rickettsia rickettsii*, *Conori australis*, *Rickettsia tsutsugamushi*.

In a second aspect the present invention provides a recombinant polynucleotide molecule comprising a sequence encoding a non-human $V_H$ region, a sequence encoding a non-human $V_L$ region, a sequence encoding a flexible linker positioned between the $V_H$ region sequence and the $V_L$ region sequence, and a heterologous sequence encoding a $C_H$ domain or epitope thereof.

By "heterologous sequence encoding a $C_H$ domain" we mean sequence encoding a $C_H$ domain which is derived from a different species than the sequences encoding the $V_H$ and $V_L$ regions.

In a preferred embodiment of the second aspect the heterologous sequence encodes a human $C_H$ domain.

By 'flexible linker' we mean a region of amino acids of sufficient length and flexibility to allow the $V_H$ and $V_L$ polypeptide regions to dock correctly with respect to each other to form an scFv fragment. The flexible linker may be a polypeptide of between 12 and 30 amino acids in length. Preferably the linker is a polypeptide of about 15 amino acids in length. The linker may have the sequence GGGGSGGGGSGGGGS.

In a preferred embodiment, the $C_H$ domain sequence is linked to the 3' end of the $V_L$ or $V_H$ sequence. In this preferred construct the chimeric antibody conjugate is synthesized as a single polypeptide chain which folds to produce two separate functional domains.

In a further preferred embodiment of the second aspect of the invention, the polynucleotide molecule includes a control sequence which directs the synthesis of both the $V_L$ and $V_H$ polypeptide regions. The control sequence is preferably an inducible promoter such as the lac promoter.

In a further preferred embodiment the polynucleotide molecule includes a sequence encoding a leader peptide which directs the synthesised polypeptide chains to the host cell periplasm. The leader sequence may be the pel B sequence.

In a third aspect the present invention provides a recombinant polynucleotide molecule comprising a sequence encoding a non-human $V_L$ region, a sequence encoding a non-human $C_L$ region, a sequence encoding a non-human $V_H$ region, a heterologous sequence encoding a $C_H$ domain or epitope thereof and optionally a sequence encoding a non-human $C_H1$ region.

In a preferred embodiment of the third aspect the heterologous sequence encodes a human $C_H$ domain.

In a further preferred embodiment of the third aspect of the present invention, the $V_L$ and $C_L$ sequences are linked together so that the $V_L$ and $C_L$ regions are expressed as a single polypeptide. In a more preferred embodiment, the $V_H$ and $C_H1$ sequences are also linked together so that the $V_H$ and $C_H1$ regions are expressed as a single polypeptide.

In a further preferred embodiment of the third aspect the polynucleotide molecule includes a control sequence which directs the synthesis of both the $V_L$-$C_L$ and $V_H$-$C_H1$ polypeptide chains. The control sequence is preferably an inducible promoter such as the lac promoter.

In a further preferred embodiment of the third aspect the polynucleotide molecule includes a sequence encoding a leader peptide which directs the synthesised polypeptide chains to the host cell periplasm. The leader sequence may be the pel B sequence. Preferably, the $V_L$-$C_L$ and $V_H$-$C_H1$ polypeptide chains associate in the host cell periplasm and are stabilised by one or more disulphide bonds between the chains.

In a further preferred embodiment of the third aspect the heterologous $C_H$ domain sequence is linked to the $V_L$-$C_L$ sequences or the $V_H$-$C_H1$ sequences so that the expressed heterologous $C_H$ domain is attached to the $V_L$-$C_L$ polypeptide or the $V_H$-$C_H1$ polypeptide.

In a further preferred embodiment of the third aspect the non-human $C_H1$ sequence is absent from the recombinant polynucleotide construct. The heterologous $C_H$ domain sequence may be linked directly to the non-human $V_H$ sequence to give rise to a chimeric non human $V_H$-human $C_H$ polypeptide chain. This chimeric polypeptide chain may associate with the non-human $V_L$-$C_L$ polypeptide chain to form a chimeric Fab fragment. It will be appreciated that such a chimeric Fab fragment will possess a specific antigen binding region, and a human constant region which provides a recognition site for class specific anti immunoglobulin antibodies.

The polynucleotide molecules of the second or third aspects of the present invention may be incorporated into plasmids or expression vectors which may then be introduced into suitable bacterial, yeast, insect or mammalian host cells.

Accordingly, in a fourth aspect the present invention provides a vector comprising a polynucleotide according to the second or third aspects of the present invention.

In a fifth aspect the present invention provides a bacterial, yeast, insect or mammalian host cell transformed with a vector according to the fourth aspect of the present invention.

In a sixth aspect the present invention provides a method of producing a chimeric antibody conjugate which comprises culturing a host cell according to the fifth aspect of the present invention under conditions enabling the expression of the conjugate and optionally recovering the conjugate.

In a seventh aspect the present invention provides a chimeric antibody conjugate produced by a method according to the sixth aspect of the present invention.

In yet another aspect of the present invention, the bifunctional molecule is able to bind to antibodies or antibody-like molecules and thereby label them with epitopes from immunoglobulin constant regions derived from different species. The complex thus formed has the properties of a specific positive antibody control: a ligand binding site with specificity for the antigen, hapten or drug in question and epitopes or domains which are recognised by immunoglobulin binding reagents. The bifunctional molecules of this aspect of the invention may be produced by recombinant DNA technology. Alternatively, recombinant fragments may be linked by conventional chemical coupling technologies.

Accordingly, in an eighth aspect the present invention provides a bifunctional molecule for use in labelling an antibody of a first species, the bifunctional molecule comprising a binding region which binds to the antibody of the first species or to one or more groups provided thereon, and a constant region derived from an antibody of a second species, the constant region comprising at least one $C_H$ domain or an epitope thereof.

The order of the binding and constant regions on the bifunctional polypeptide is not critical. The order may be either (N terminus)-binding region-constant region-(C terminus) or vice versa, ie (N terminus)-constant region-binding region-(C terminus).

In a ninth aspect the present invention provides a complex formed between (i) an antibody or biologically active fragment thereof derived from a first species and (ii) a bifunctional molecule, the bifunctional molecule comprising a binding region which binds to the antibody of the first species or to one or more groups provided thereon, and a constant region derived from an antibody of a second species, the constant region comprising at least one $C_H$ domain or an epitope thereof.

By "biologically active fragment" we mean a fragment which mimics the binding of the antibody derived from the first species to at least one antigenic determinant.

In a preferred embodiment of the eighth and ninth aspects, the binding and constant regions of the bifunctional molecule are separated by a linker molecule. The linker molecule may be a short peptide. Preferably, the linker molecule is a peptide of between 1 and 20 amino acids in length, more preferably between 1 and 10 amino acids in length, and more preferably between 2 and 5 amino acids in length.

In a further preferred embodiment of the eighth and ninth aspects, the binding region is not derived from an antibody. By this we mean that the binding region is preferably not (i) a Fab fragment, (ii) a portion of a Fab fragment, (iii) an ScFv fragment or (iv) a portion of an ScFv fragment.

In one embodiment of the eighth and ninth aspects, the binding region binds directly to the antibody derived from the first species.

In a further preferred embodiment of the eighth and ninth aspects, the binding region is derived from a protein selected from the group consisting of *Streptococcal* protein G (described in Björck and Kronvall (1984), and Boyle and Reis (1987), the entire contents of which are incorporated herein by reference) *Staphylococus aureus* protein A (described in Uhlen et al. (1984), and Boyle and Reis (1987), the entire contents of which are incorporated herein by reference) and *Peptostreptococcus magnus* protein L (which is described in Åkerström and Björck (1989), the entire contents of which is incorporated herein by reference). In a further preferred embodiment, the binding region comprises one of the immunoglobulin binding regions of *Staphylococcus aureus* protein A. The immunoglobulin binding region of *Staphylococcus aureus* protein A may be fragment B.

In a further preferred embodiment of the eighth and ninth aspects, the binding region comprises a mouse Fc γ receptor or fragment thereof. The mouse Fc γ receptor may be selected from the group consisting of FcγRI, which specifically binds monomeric mouse IgG2a; FcRII, which binds aggregated IgG1, IgG2a and IgG2b; and FcγRIII, which binds the minor subclass IgG3 (see Heusser et al., 1977; Segal et al., 1978; Unkeless et al., 1988; Hogarth et al., 1987; Kulczycki et al., 1990, the entire contents of which are incorporated herein by reference).

In another preferred embodiment of the eighth and ninth aspects, the binding region comprises a histidine rich glycoprotein (as described in Borza et al., 1996 and Gorgani et al., 1997, the entire contents of which are incorporated herein by reference).

In another embodiment of the eighth and ninth aspects, the binding region binds to one or more groups provided on the antibody of the first species. Preferably, the group(s) is a biotin molecule and the binding region comprises streptavidin (described in Argaraña et al. (1986). U.S. Pat. No. 5,672,691 and U.S. Pat. No. 5,489,528, the entire contents of which are incorporated herein by reference) or a fragment thereof.

In a further preferred embodiment of the eighth and ninth aspects of the present invention, the first species is a rat or a mouse.

In a further preferred embodiment of the eighth and ninth aspects, the antibody of the first species is a monoclonal antibody. In a further preferred embodiment, the antibody of the first species is an IgG antibody.

In a further preferred embodiment of the eighth and ninth aspects, the antibody constant region is not a naturally occurring Fc fragment.

In a further preferred embodiment of the eighth and ninth aspects, the antibody constant region comprises or consists of a non-naturally occurring combination of immunoglobulin $C_H$ domains or epitopes thereof. The constant region may include or consist of two $C_H$ domains of the same type, for example, two $C_H3\mu$ domains. Alternatively, the constant region may include or consist of two different domains. The two different domains, or epitopes thereof, may be derived from antibodies of different classes. In a preferred embodiment, the constant region consists of a single $C_H$ domain.

In a further preferred embodiment of the eighth and ninth aspects, the second species is a human. It will be appreciated, however, that the second species may be non-human (for example, bovine, canine, ovine, equine, feline or caprine) in cases where the bifunctional molecule or complex is to be used as a positive control reagent in assays involving sera derived from non-human species.

In a particularly preferred embodiment of the ninth aspect of the present invention, the bifunctional molecule is suitable for combination with mouse IgG as a positive IgM control and the constant region comprises one or more $C_H3\mu$ domains.

In a particularly preferred embodiment of the ninth aspect of the present invention, the bifunctional molecule is bound to a location on the antibody (or fragment thereof) of the first species which does not significantly hinder the binding between the antibody (or fragment thereof and its specific antigen.

In a further preferred embodiment of the complex according to the ninth aspect, the affinity between the binding region and the antibody or biologically active fragment thereof derived from the first species is sufficient to form a stable complex in solution. Preferably, the binding region has a $K_D$ for the antibody of less than $10^{-6}$ M. More preferably, the $K_D$ is less than $10^{-8}$ M and more preferably less than $10^{-9}$ M.

In a further preferred embodiment of the eighth and ninth aspects, the antibody constant region is modified in order to facilitate the production of the molecule, or to reduce aggregation of individual bifunctional molecules, without substantially altering the characteristic epitopes of the domain. For example, a cysteine residue usually associated with the formation of an inter-chain disulphide bond may be mutated to serine. In another example, a bifunctional molecule which contains a fragment of *Staphylococcal* protein A linked to a human Cγ3 domain may aggregate because of the high affinity of the protein A fragment for human IgG constant domains. This aggregation may be circumvented by a substitution His to Arg at position 435. Evidence suggests that the lack of binding of protein A to human IgG subclass 3 is related to the substitution of Arg for His at position 435 (see Deisenhofer, 1981, the entire contents of which are incorporated herein by reference).

It will be appreciated by persons skilled in the art that within the context of the present invention, the preferred $C_H$ domains or epitopes will be dependent on the intended use of the bifunctional molecule. For example, if the bifunctional molecule or complex is to be used as a replacement for positive IgM control sera, the preferred $C_H$ domains or epitopes will be $C_H\mu$ domains or epitopes. Alternatively, if the bifunctional molecule or complex is to be used as a replacement for positive IgG control sera, the preferred $C_H$ domains or epitopes will be a $C_H\mu$ domains or epitopes. If the bifunctional molecule or complex is to be used as a replacement for positive IgA control sera, the preferred $C_H$ domains or epitopes will be a $C_H\alpha$ domains or epitopes.

In a tenth aspect, the present invention provides an isolated polynucleotide encoding a bifunctional molecule according to the eighth aspect of the present invention.

The polynucleotide molecule of the tenth aspect of the present invention may be incorporated into plasmids or expression vectors which may then be introduced into suitable bacterial, yeast, insect or mammalian host cells.

Accordingly, in en eleventh aspect the present invention provides a vector comprising a polynucleotide according to the tenth aspect of the present invention.

In a twelfth aspect the present invention provides a bacterial, yeast, insect or mammalian host cell transformed with a vector according to the eleventh aspect of the present invention.

In a thirteenth aspect the present invention provides a method of producing a bifunctional molecule which comprises culturing a host cell according to the twelfth aspect of the present invention under conditions enabling the expression of the bifunctional molecule and optionally recovering the bifunctional molecule.

In a fourteenth aspect the present invention provides a bifunctional molecule produced by a method according to the thirteenth aspect of the present invention.

In a fifteenth aspect the present invention provides a method of producing a complex according to the ninth aspect which comprises admixing an antibody or biologically active fragment thereof derived from a first species with a bifunctional molecule according to the eighth aspect of the present invention.

Methods for detecting antibodies in biological samples are well known. In general, these methods involve incubation of the sample with (i) a antigenic determinant characteristic of a particular disease and (ii) an anti human Ig antibody. The antibody measurement is generally compared to a control measurement obtained by incubating the antigenic determinant characteristic of the disease and the anti human Ig antibody with a positive control serum obtained from an individual with the disease. The present inventors have found that the chimeric antibody conjugates of the present invention react in diagnostic tests in a manner similar to class specific positive control serum.

Accordingly, in a sixteenth aspect the present invention provides a method for detecting an antibody in a biological sample which involves comparing the level of detection obtained with the biological sample to the level of detection obtained with a positive control, wherein the positive control comprises a chimeric antibody conjugate according to the first aspect, or a complex according to the ninth aspect.

In a preferred embodiment of the sixteenth aspect of the present invention, the biological sample is a human biological sample.

In a further preferred embodiment of the sixteenth aspect of the present invention the antibodies to be detected are antibodies characteristic of a disease selected from but not limited to dengue fever, Japanese encephalitis, rubella, spotted fever, herpes infection, parvovirus infections, melioidosis, typhoid, leptospirosis, malaria, yellow fever, whooping cough, systemic candidiasis/thrush, chicken pox, shingles, AIDS, hepatitis, liver cancer, cervical cancer, infectious mononucleosis, nasopharyngeal carcinoma, Ross River fever, brucella, exanthum subitum (Sixth disease/Roseola infantum), erythema ingfectiosum (Fifth disease), Q Fever, cold sores, genital herpes, spotted fever, scrub typhus.

The antibody to be detected in the biological sample may be an antibody of any class. In a preferred embodiment, however, the antibody is an IgM antibody.

The terms "comprise", "comprises" and "comprising" as used throughout the specification are intended to refer to the inclusion of a stated component or feature or group of components or features with or without the inclusion of a further component or feature or group of components or features.

The invention will now be described in detail by reference to the following non-limiting Figures and Examples.

BRIEF DESCRIPTION OF THE FIGURES

FIG. 3 shows in cartoon form the two regions of the bifunctional binding molecule and illustrates one embodiment of the invention. Also shown is the complex formed between the bifunctional molecule and intact mouse IgG in which the mouse IgG is decorated with antibody C domains, preferably from human immunoglobulin heavy chains.

FIG. 4 shows a further embodiment of the invention in which a complex is formed between the bifunctional molecule and one or more groups introduced onto the antibody of species A. In the embodiment illustrated, the group is biotin, the first region which binds to the group is streptavidin or a fragment thereof and the antibody is mouse IgG.

FIG. 5 illustrates in cartoon form the structure of the bacterial expression plasmid containing the sequence of one embodiment of the invention. The expression cassette contains a chemically inducible promoter, lac, followed by sequence encoding the components of the chimeric protein. The pel B sequence directs the synthesised protein to the cell periplasm, the $V_H$ and $V_L$ regions joined by linker sequence are the mouse scFv antibody, and $C_H$ is the human immunoglobulin constant domain sequence inserted between the Not I and Sac II sites. FLAG is an octapeptide recognition sequence recognised by the antibody anti FLAG® M2 (Eastman Kodak Co., New Haven, Conn.) used for monitoring expression; stop designates a stop codon and TT designates a transcription terminator. The remainder of the vector is derived from vector pUC19 (Yanisch-Perron et al., 1985). The entire vector minus the specific inserts is denoted pGC (Coia et al., 1996)

FIG. 6 illustrates the reactivity in ELISA of the 4 different human IgM $C_H$ domain constructs linked to the scFv 1C3 (anti-glycophorin). With glycophorin bound to the ELISA well, samples containing the gene product were introduced and incubated for 1 hour at RT. After extensive washing, wells were probed with polyclonal anti human IgM antiserum raised in sheep and labelled with horseradish peroxidase. After 1 hour incubation at RT and extensive washing, ABTS was added for colour development which was read at 405 nm after 20 mins.

FIG. 7 illustrates the reactivity in a dengue IgM capture ELISA of unfractionated periplasm taken from an expression culture of the 13C11 (anti dengue)scFv-$C_H3\mu$ domain construct. Positive, negative and calibrator controls were supplied with the test kit (see text) and used as directed: (100 μl per assay) at a dilution of 1/100 in serum diluent. Other reagents were as supplied with the kit. Periplasm was diluted 1/5, 1/10, 1/50 and 1/100. 100 μl of each dilution including undiluted periplasm were added to test wells on the ELISA plate, covered and incubated for 1 hour at 37° C. After 4 washes with diluted wash buffer, 100 μl of a combined mixture of stablized dengue virus antigens with peroxidase labelled anti-dengue monoclonal antibody were added and the plate further incubated for 1 hour at 37° C. After 6 washes with diluted wash buffer, 100 μl TMB solution was added and colour development proceeded for 10 mins. 100 μl Stop solution was then added and the colour read at 450 nm.

Negative, Calibrator and Positive refer to serum controls supplied with the test. Peri, peri 1/5-peri 1/100 refer to test samples containing the 13C11 (anti dengue)scFv-$C_H3\mu$ domain construct. Peri neg control is derived from a culture of 1C3(antiglycophorin)-$C_H3\mu$ domain chimera (Example 1).

FIG. 8 shows the DNA sequence of the expression cassette (from pGC vector) containing fragment B from *Staphylococcus aureus* Protein A joined via a short linker to the human IgM heavy chain $C_H3\mu$ domain, together with a terminal FLAG® tag sequence, pel B leader and trp A terminator.

FIG. 9 shows in cartoon form the constituents of the ELISA used to demonstrate the binding of various mouse IgG subclasses to the bifunctional linking reagent described in Example 1 which has bound to immobilised polyclonal anti human IgM antibody, raised in sheep.

FIG. 10 shows the verified sequence of an expression cassette in pGC comprising the pel B leader sequence, core streptavidin, human IgM $C_H3$ domain and FLAG® tag.

FIG. 11 shows results from size exclusion chromatography on Superdex200 of a sample containing refolded Streptavidin-$C_H3\mu$ in phosphate buffered saline. Flow rate was 0.5 ml/min.

DETAILED DISCLOSURE OF THE INVENTION

In one aspect the present invention relates to a recombinant chimeric antibody molecule. One region of this chimeric molecule comprises an antigen binding region derived from an antibody.

Fragments of antibody molecules containing predominantly antigen binding regions have been synthesized using prokaryote or lower eukaryote expression systems (eg bacterial or yeast cells) (see, for example, PCT/AU93/00491, the entire disclosure of which is incorporated herein by reference). The antigen binding site is composed of amino acid residues formed in up to six surface loops at the extremity of the molecule. The loops on the outer domain are termed complementarity determining regions (CDRs) and provide the specificity of binding of the antibody to the antigenic target, by variation in the amino acid composition of these surface loops. The antigen binding regions of both intact IgG and sub-fragments are illustrated in FIG. 1.

In order to stabilise the paired associations of the $V_H$ and $V_L$ regions produced by such cultures, these regions may be expressed as one continuous polypeptide chain where there is a region of amino acids of sufficient length and flexibility interspersed between the C-terminus of one domain and the N-terminus of the other to allow the two domains to dock correctly with each other to correctly position the CDR loops. Methods of manufacture of covalently linked single chain Fv fragments are disclosed in U.S. Pat. No. 4,946,778, U.S. Pat. No. 5,132,405 and WO 94/07921 the entire contents of which are incorporated herein by reference.

Alternatively, the antigen binding domains can be produced as Fab fragments where two polypeptide chains $V_H$-$C_H1$ and $V_L$-$C_L$ are synthesised separately from mouse gene sequences and the subsequent formation of heavy and light chain fragment pairs are stabilised by a disulphide bond between the two chains. (See, for example, Better et al., 1988, Skerra, 1993, Dolezal et al., 1995, the entire contents of which are incorporated herein by reference). A preferred source of paired $V_H$ and $V_L$ genes for the formation of antigen binding domains is cDNA prepared from mRNA isolated from mouse monoclonal antibody cell lines.

In one preferred embodiment the chimeric antibody conjugate is a polypeptide chain which, when expressed in *E. coli*, yeast or mammalian cells from a single gene construction, folds to produce two separate functional domains, as shown in FIG. 2. The first domain binds a specific antigen, and the second domain contains a specific immunoglobulin constant domain sequence (epitope) which may be recognised and bound by antibodies, prepared in rabbits, sheep or other such animal, by immunisation with class specific human immunoglobulins.

Figure 1:
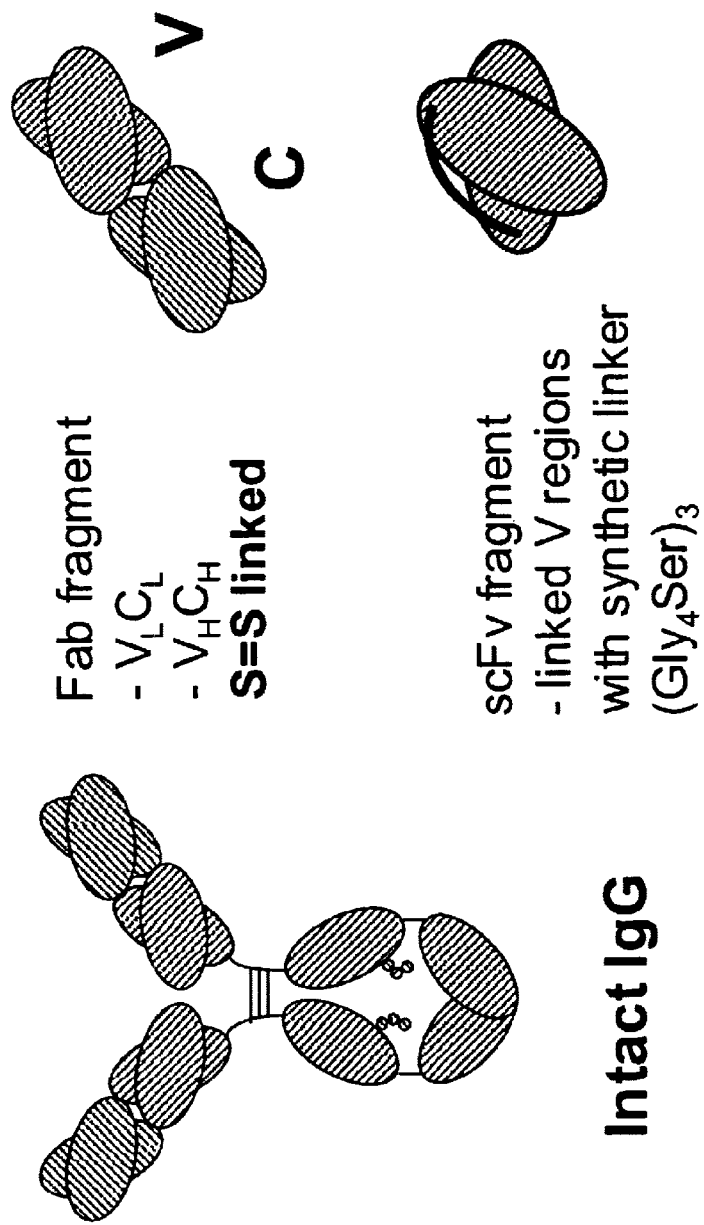
FIG. 1 shows the structure of intact IgG antibody (a) along with the two sub fragments capable of being produced in prokaryotic or lower eukaryotic cells, Fab (b) and scFv (c). The antigen binding region, the location of the CDR loops are indicated.
Figure 2:
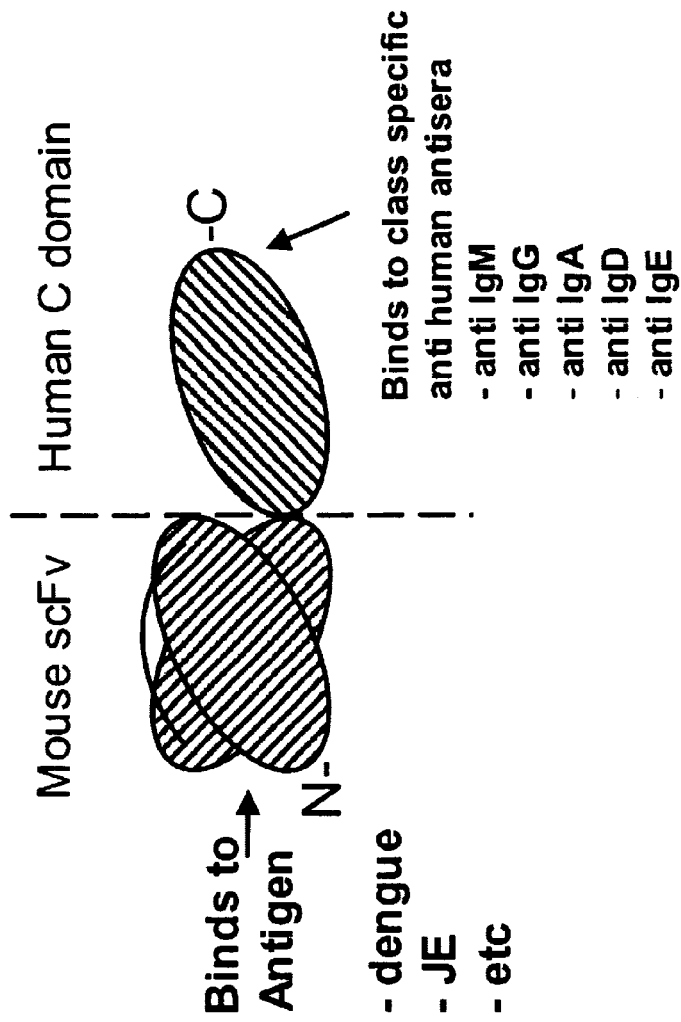
FIG. 2 illustrates one embodiment of the invention. The single polypeptide chain protein folds into two domains. The scFv region derived from mouse DNA sequences folds to form the specific antigen binding site. The C-domain derived from human DNA sequences of immunoglobulin constant regions folds to provide binding epitopes for heterologous, class specific anti human immunoglobulin sera.
Figure 4:
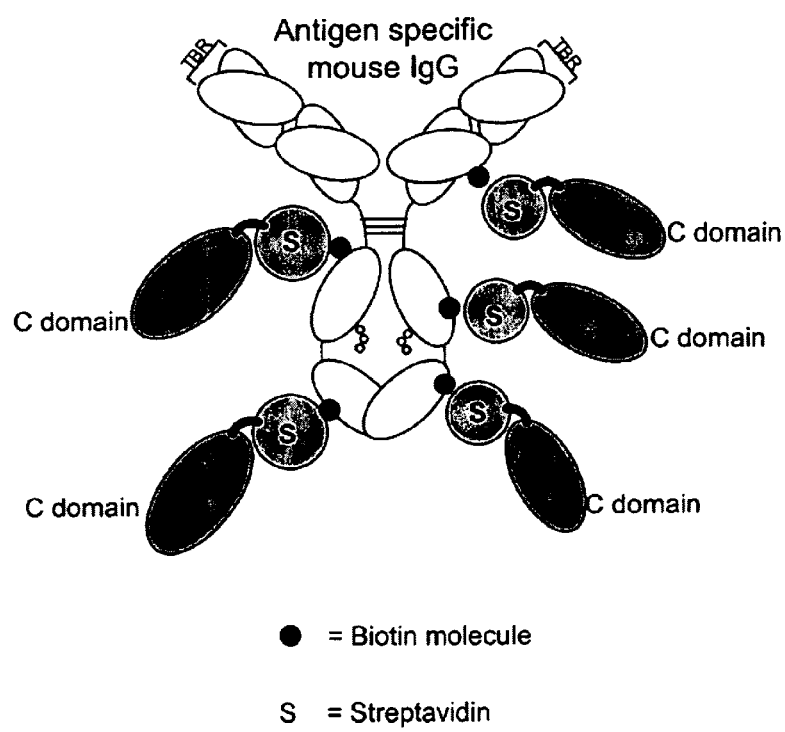
Figure 5:
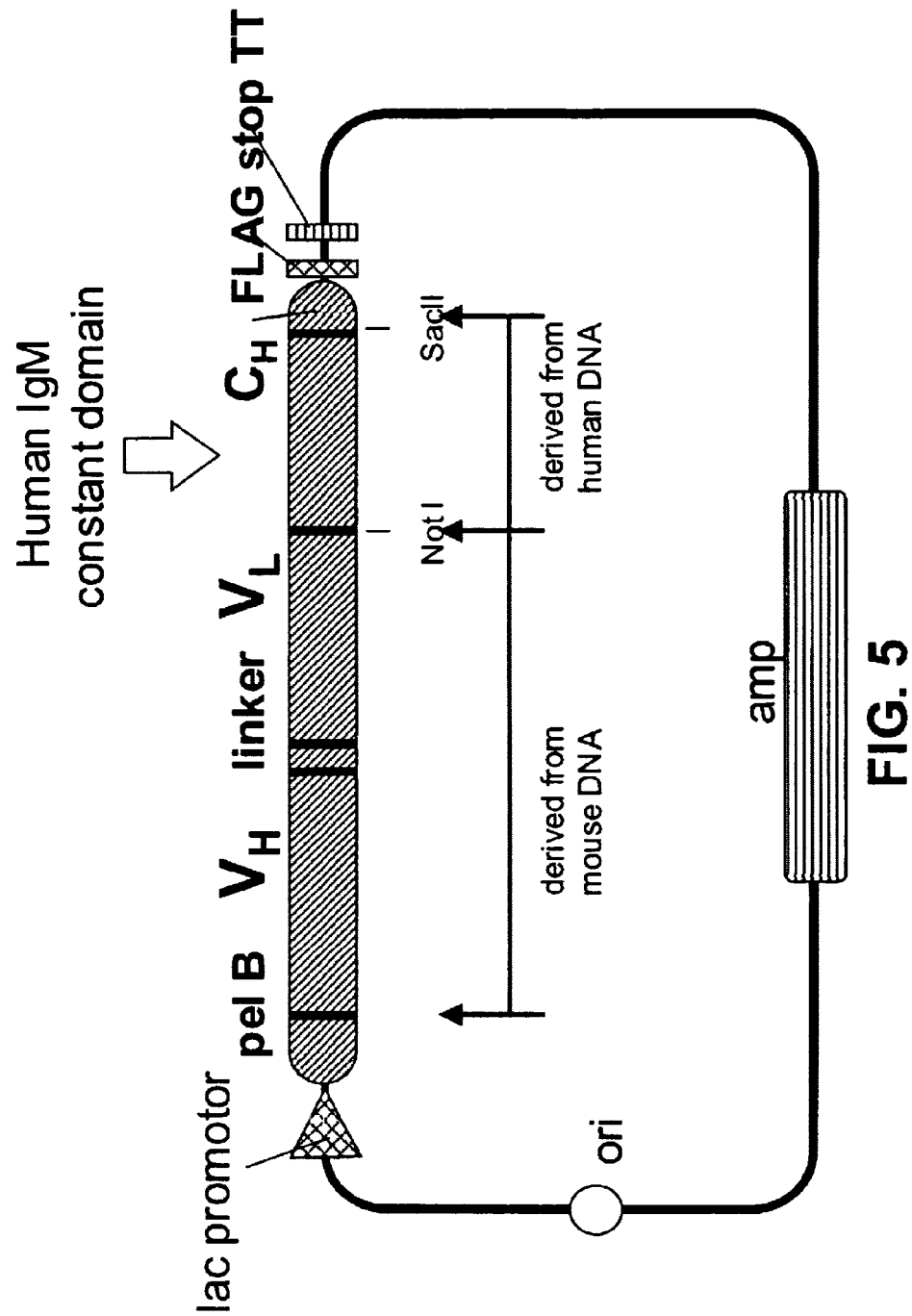
Figure 6:
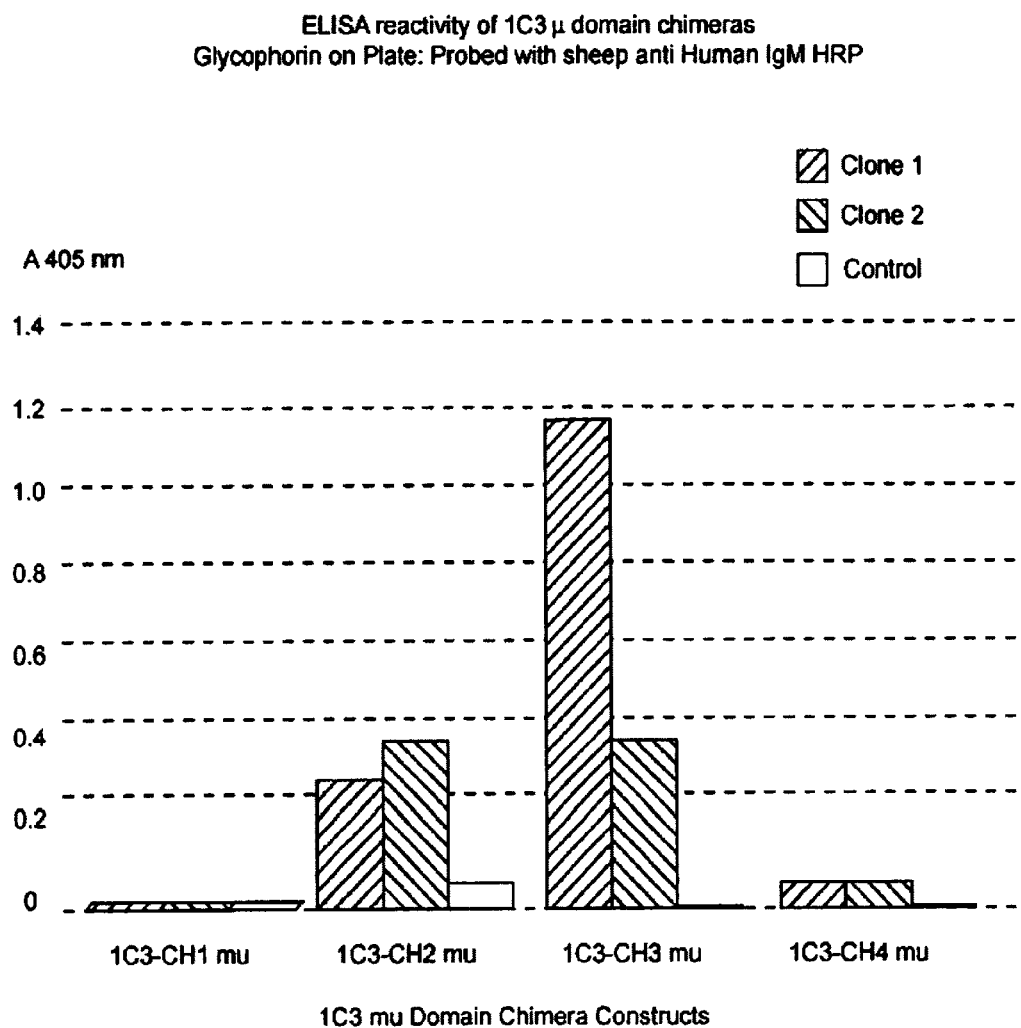
Figure 7:
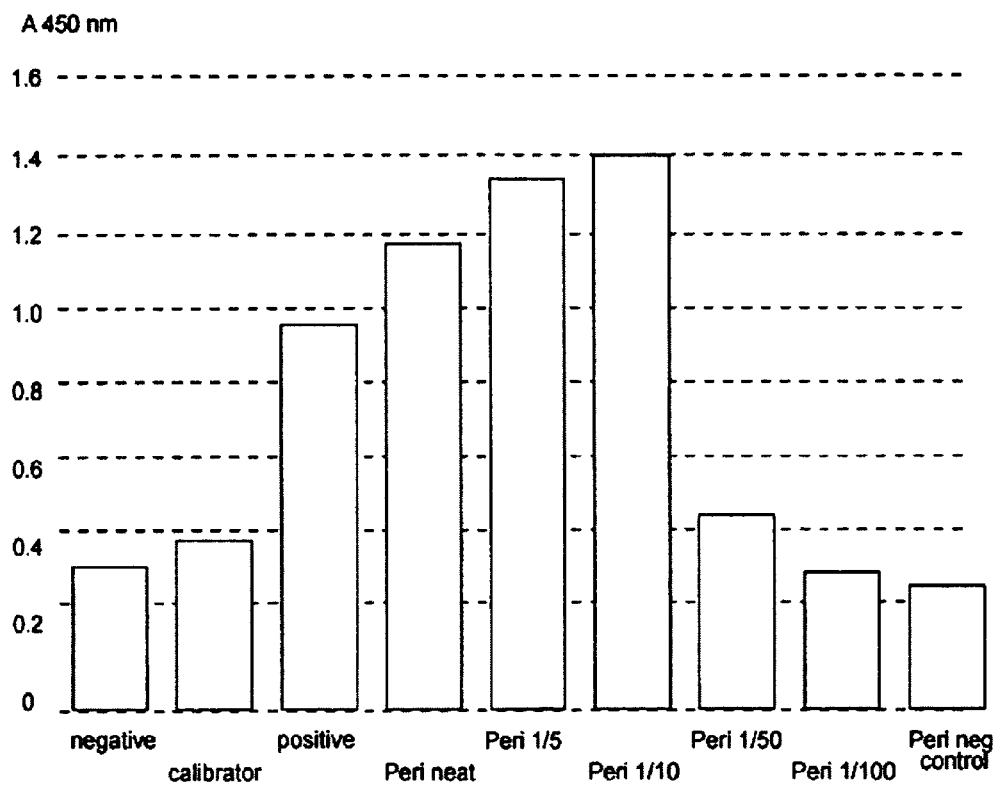

The first functional domain may consist of an antigen binding domain, formed by paired antibody $V_H$ and $V_L$ regions either a) linked in active conformation via a flexible peptide linker as in a scFv molecule or b) linked to mouse $C_H$ and $C_L$ domains as in a Fab antibody fragment. The flexible linker used to link the $V_H$ and $V_L$ regions as in a scFv molecule may be a polypeptide of between 12 and 30 amino acids in length (Huston et al., 1991). The $V_H$ and $V_L$ gene sequences which code for the antibody $V_H$ and $V_L$ regions may be amplified via PCR from cDNA of non-human origin (usually prepared from a mouse monoclonal antibody cell line producing antibody with binding specificity for the antigen being assayed in the diagnostic test in question). Any antigen binding specificity may be incorporated in this domain in either the Fab or scFv conformation. Preferably, a mouse monoclonal antibody cell line exists with that specificity or a $V_H/V_L$ pair has been selected from an antibody phage library with binding specificity for that particular antigen.

The second functional domain may consist of either a single heavy chain constant domain or several in tandem which display binding sites (epitopes) for class specific polyclonal anti immunoglobulin antisera, also known as capture antibodies. The $C_H$ region gene sequences may be amplified via PCR from cDNA prepared from mRNA isolated from peripheral blood lymphocytes. The $C_H$ regions can be from any of the immunoglobulin heavy chain genes, (those for IgM, IgG, IgA, IgD, IgE) and the gene product from the particular $C_H$ region is bound by the class specific anti immunoglobulin antiserum.

It will be appreciated that chimeric antibody conjugates of the present invention are capable of reacting in diagnostic tests in a manner similar to a class specific positive control serum. The chimeric conjugate will bind to a specific antigen, and will in turn be bound by the class specific capture antibodies which determine its immunoglobulin. An advantage of the conjugates of the present invention is that they may be produced in large quantities, free of contaminants, by recombinant DNA technology.

In yet another aspect the present invention relates to a bifunctional molecule which is able to bind to antibodies or antibody-like molecules and thereby label them with epitopes from immunoglobulin constant regions derived from different species. Preferably, the bifunctional molecule is a single polypeptide chain which when expressed in *E. Coli*, yeast or mammalian cells folds to produce two separate functional domains, as shown in FIG. 3. The first domain preferably binds to a specific region of an antibody, for example, mouse IgG, and the second domain contains a specific immunoglobulin constant domain sequence (epitope) which may be recognised and bound by antibodies, prepared in rabbits, sheep or other such animal, by immunisation with class specific human immunoglobulins.

The affinity of binding between the binding region and antibody is preferably sufficient to form a stable complex in solution between mouse IgG and the bifunctional molecule. The region on the antibody to which the bifunctional molecule binds is preferably in a location which will not sterically hinder the binding between the mouse IgG antibody binding site and its specific antigen.

In one embodiment. the binding region binds to a group provided on the antibody. This particular embodiment is illustrated in FIG. 4, in which the binding region comprises streptavidin or a fragment thereof and the antibody is mouse IgG.

The intention will be described in detail by reference to the following non-limiting examples.

EXAMPLE 1

Production of a C-domain (IgM) extended scFv

The gene sequences of the four constant domains (C domains) of human IgM heavy chain were separately amplified from cDNA prepared from mRNA isolated from human peripheral blood lymphocytes using polymerase chain reaction techniques. The design of the oligonucleotide primers used in the amplifications was based upon the 5' and 3' base sequence of each of the four IgM heavy chain exons, obtained through GENBANK accession X14940 (Dorai and Gillies, 1989).

In the primers, specific restriction enzyme recognition sequences were added (NotI at the 5' end and SacII at the 3' end) to each exon sequence to facilitate the introduction of the C domain sequence at a specific site in a previously constructed plasmid expression vector. The expression cassette of this *E. coli* plasmid vector (pGC; Coia et al., 1996) contained $V_H$ and $V_L$ sequences from the mouse monoclonal antibody cell line 1C3, (Rylatt et al., 1990, W091/04492) with binding specificity for human glycophorin. These were arrayed in the scFv format, with the 3' end of the $V_H$ sequence linked to the $V_L$ sequence via a 45 bp sequence which coded for the protein sequence GGGGSGGGGSGGGGS. In the synthesized protein, this flexible linker region allows the correct docking of $V_H$ with $V_L$. The site for the introduction of the heavy chain exon was at the 3' end of the mouse $V_L$ sequence without any intervening sequence, save that for the restriction sites, as shown in FIG. 5. Fragments were ligated together using the normal protocols and the ligation mix used to transform *E. coli* strain XL1-Blue by electroporation.

Recombinant protein was produced from positively transformed colonies of the four different constructions (each with a different IgM C-domain sequence) by induction of the plasmid lac promoter with 0.5 mM IPTG in log phase cultures grown at 30° C. After a further 4 hours incubation at 25° C. the cell pellet was harvested by centrifugation, and the contents of the cell periplasm isolated using the protocol of Minsky et al. (1986).

The periplasmic fraction was assayed by ELISA for the presence of protein molecules with the following properties—1) the ability to bind to immobilised glycophorin on the ELISA plate and 2) a target for the binding of horseradish peroxidase-labelled polyclonal anti human IgM serum (prepared in sheep. Silenus Laboratories, Melbourne Australia). The results in FIG. 6 show that the construction with IgM constant domain 3 ($C_H3\mu$) gave the strongest reaction with the labelled polyclonal antiserum to human IgM. This was followed by domain $C_H2\mu$, with domains $C_H4\mu$ and $C_H1\mu$ showing the weakest reactions. It was a surprising observation that the majority of the reactivity of the polyclonal antiserum was directed to one domain of the IgM heavy chain. Thus, for this particular polyclonal antiserum directed against human IgM, the construct scFv-$C_H3\mu$ is a molecule with the preferred properties of a substitute for a positive human serum control.

A scFv with binding specificity for human glycophorin was solely used to demonstrate the present invention. As will be appreciated by persons skilled in this field, the antigen binding portion of the conjugate may be replaced with binding specificities to other antigenic entities which are the focus of a wide range of diagnostic test applications.

EXAMPLE 2

Construction of extended scFv (13C11 antidengue) linked to a human IgM C domain The reagent was produced from a DNA construct in which the coding region for a mouse scFv directed against dengue virus was genetically linked to that of the third constant domain of human IgM heavy chain ($C_H3\mu$). cDNA was prepared from MRNA isolated from the mouse monoclonal antibody cell line 13C11, which specificity for Dengue virus surface antigens (Queensland University of Technology and PanBio Pty Ltd.). Immunoglobulin $V_H$ and $V_L$ domain DNA sequences were amplified from the cDNA using polymerase chain reaction and oligonucleotide primer sets according to Zhou et al. (1994). These were linked in the scFv format $V_H$ -linker-$V_L$, where the linker was a 45 bp nucleic acid sequence coding for the protein sequence GGGGSGGGGSGGGGSGGGGS. The resultant fragment was digested with restriction endonucleases Nco I and Not I and purified by agarose gel electrophoresis. The expression vector as described in Example 1 which contained the 1C3 (antiglycophorin) scFv-$C_H3\mu$ domain sequence was also digested with Nco I and Not I to excise the coding sequence for the 1C3 scFv. The remainder of the vector (plus C domain coding sequence) was purified and ligated with the digested 13C11 (anti dengue) scFv coding region using standard protocols. This ligated DNA was then used to transform *E. coli* strain XL1-Blue by electroporation. Positive colonies were verified both by DNA sequencing and small scale protein expression.

*E. coli* strain TOPP6 (Stratagene. La Jolla, Calif.) was transformed with purified plasmid DNA from a verified clone and used for protein expression. 500 ml of 2xYT medium (1.0% Yeast extract, 1.6% Bacto Tryptone, 1.0% NaCl) supplemented with ampicillin at 200 μg/ml was inoculated with an overnight culture of the transformed TOPP6 cells and incubated at 37° C. with agitation until the $A_{600}$ had reached 1.0. IPTG (isopropylthiogalactoside) was added to a concentration of 0.5 mM to induce the expression of the chimeric gene construct. The culture was shaken for a further 4 hours at a 25° C. Cells were harvested by centrifugation and the periplasmic contents isolated using the protocol of Minsky et al. (1986).

Dilutions of the unfractionated periplasm were analysed in the Dengue IgM Capture ELISA kit (PanBio Ltd, Windsor, QLD, Australia: Sang et al., 1998) using positive, negative and calibrator serum controls as supplied in the kit. In the assay, human IgM antibodies are captured by surface bound polyclonal anti human IgM antiserum (Silenus), and incubated with soluble dengue antigens plus a peroxidase labelled, dengue antigen-specific monoclonal antibody, to reveal the presence of dengue specific antibodies.

The results are shown in FIG. 7. The periplasm fractions reacted positively, with the neat, ⅕ and 1/10 dilutions giving higher absorbance readings at 450 nm than the normal control. At 1/50, the periplasm still gave an absorbance reading greater than the calibrator control, which marks the cut-off between positive and negative reactions. It was calculated that an absorbance reading equivalent to the positive control would have been obtained from a periplasm dilution of 1/30. Periplasm from a culture of an unrelated chimera (1C3-$C_H3\mu$, anti-glycophorin, see Example 1) showed no positive reaction in this test.

EXAMPLE 3

Construction of Extended scFv (13C11 anti dengue) linked to a human IgG C-domain The gene sequences of human IgG constant domains 2 and 3 were separately amplified from cDNA from mRNA isolated from human peripheral blood lymphocytes using polymerase chain reaction techniques. The design of the oligonucleotide primers used in the amplifications were based upon the 5' and 3' sequences for each of the heavy chain exons, obtained through Genbank accession no E06998.

Sequences coding for NotI and SacII restriction sites were added to the 5' and 3' end respectively of the $C_H2\gamma$ and $C_H3\gamma$ sequences to enable the insertion into pGC 13C11-$C_H3\mu$ from which the $C_H3\mu$ sequence had been removed as a NotI-SacII fragment.

Expression in *E. coli* and purification of product was performed as described in Example 2. The presence of product in the periplasmic fraction was confirmed by analysis of samples by polyacrylamide gel electrophoresis and Western blotting, probing the FLAG® tag using mouse anti FLAG® M2 antibody (Hopp et al., 1988) The products were denoted 13C11$C_H2\gamma$ and 13C11$C_H3\gamma$ respectively.

PanBio Indirect Dengue ELISA using 13C11CH2γ and 13C11CH3γ

Periplasmic samples containing 13C11$C_H2\gamma$ and 13C11$C_H3\gamma$ were diluted 1/10 in PBS/0.05% Tween 20 and 100 μl loaded in duplicate on an ELISA plate coated with dengue antigens (PanBio Dengue Indirect ELISA Kit Cat DET500) and incubated for 1 hour at 37° C. Controls included PBS/Tween 20 as negative control and positive IgG control serum which was probed with both anti human IgM and IgG antibodies. After 6 washes with PBS/0.05% Tween20, samples and controls were then probed with either sheep anti human IgM or IgG labelled with horseradish peroxidase (Silenus/AMIRAD, Melbourne) at 1:1000 dilution in PBS/0.05% Tween20. The plate was incubated at 37° C. for 1 hour then washed 6 times as previously. 100 μl TMB reagent, supplied with the kit, was added to each well, the plate incubated at room temperature for 10 min. then the reaction was stopped by the addition of 100 μl 1M phosphoric acid. Colour intensity was read at 450 nm. The results are shown in Table 1.

TABLE 1

| | Absorbance 450 nm | |
|---|---|---|
| | HRP-anti Human IgG | HRP-anti Human IgM |
| 13C11 CH3γ Periplasm 1/10 | 1.684, 1.670 | 0.111. 0.109 |
| 13C11 CH2γ Periplasm 1/10 | 0.500. 0.586 | 0.133. 0.113 |
| Human IgG (Dengue Positive) 1/100 | 0.971. 0.940 | 0.202. 0.361 |
| PBS/0.05% Tween 20 | 0.308. 0.261 | 0.112. 0.275 |

Both 13C11$C_H3\gamma$ and 13C11$C_H2\gamma$ extended scFvs show a positive reaction above background in this ELISA, the results with the 13C11$C_H3\gamma$ periplasm being comparable or better than the Human IgG dengue positive control. The reaction with the construct containing the human IgG $C_H3\gamma$ domain gave a stronger response than with the CH2γ domain, indicating that extended scFvs with a $C_H3\gamma$ domain would be the preferred construct for use as a replacement IgG positive control.

EXAMPLE 4

Production of a bifunctional molecule containing the B fragment of *Staphylococcal* Protein A linked to a human IgM C-domain (FB-$C_H3\mu$)

The gene sequence for fragment B of Protein A (FB) from *Staphylococcus aureus* was amplified from chromosomal DNA prepared from strain ATCC 25923 using polymerase chain reaction techniques. The design of the oligonucleotide primers used in the amplification was based upon the 5' and 3' base sequences as reported by Uhlen et al. (1984), also GENBANK accession J01786. In the primers specific restriction enzyme recognition sites were added NcoI at the 5' end and NotI at the 3' end to facilitate the introduction at a specific site in a previously constructed plasmid expression vector (pGC: Coia et al., 1996).

In this vector the sequence encoding a human IgM C domain ($C_H3\mu$) had previously been inserted as a NotI-SacII fragment. A short sequence encoding the three amino acids Ser, Asp, Pro was included downstream of the FB fragment and before the Not I site to introduce some flexibility between the FB domain and the human $C_H3\mu$ domain. The Human $C_H3\mu$ domain had previously been amplified from cDNA prepared from mRNA isolated from human peripheral blood lymphocytes using polymerase chain reaction techniques, using oligonucleotides based upon the 5' and 3' sequences of the domain obtained through GENBANK accession X14940 (Dorai and Gillies, 1989). We have demonstrated herein that human IgM C domain 3 ($C_H3\mu$) contains the major reactive epitopes which are bound by several polyclonal and monoclonal anti human IgM antisera capture reagents. Fragments were ligated together using standard ligation protocols and the ligation mix then used to transform E. coli strain XL1 Blue by electroporation. The complete DNA sequence of the expression cassette comprising the pel B leader sequence, fragment B of S. aureus Protein A, human $C_H3\mu$ domain, and FLAG® (a tag recognition sequence, Hopp et al., 1988) was verified by using automatic DNA sequencing methods and is shown in SEQ ID NO: 2 and FIG. 8.

Recombinant protein was produced from positively transformed E. coli colonies by induction of the lac promoter with 0.2mM IPTG (isopropyl β-d-thio galactoside) in log phase cultures grown at 37° C. Cultures were induced at a $A_{600}$ of 1.5–2 and incubated for a further 16 hours at 18° C. The cell pellet was then harvested by centrifugation and the contents of the cell periplasm isolated using the protocol of Minsky et al. (1986).

Analysis of the periplasmic fraction by polyacrylamide gel electrophoresis and Western blot probed with mouse anti FLAG® M2 antibody revealed the presence of a FLAG-tagged component in the periplasm with an approximate molecular weight (Mr) of 20 kD. The periplasmic fraction was then assayed by ELISA to reveal the presence of protein molecules with the following properties:

1. The ability to bind to polyclonal anti human IgM antibody prepared in sheep and immobilised on the ELISA.
2. The ability to bind to intact mouse IgG as detected by the addition of goat anti mouse IgG antibody, labelled with horseradish peroxidase which reacts with TMB (3',3',5',5'-tetramethylbenzidine) to produce a coloured product measured at 450 nm.

Property 1 was demonstrated by an ELISA in which crude periplasm was reacted with immobilised polyclonal anti human IgM capture antibody, then probed with mouse anti FLAG® antibody together with goat anti mouse IgG labelled with horseradish peroxidase to detect the C terminal FLAG tag. ELISA plate wells were coated with polyclonal sheep anti human IgM antiserum (Sang et al., 1998), blocked with 5% Skim milk powder in PBS at 37° C. for 1.5 hours. Between each addition step, the wells were washed 10 times with PBS-0.05% Tween 20. Each addition (100 µl) was incubated for 20 min at room temperature. Mouse anti FLAG® (Eastman Kodak Co. New Haven, Conn.) was used at 1 µg/ml in PBS-0.05% Tween 20. Goat anti mouse IgG Fc-HRP was used at 0.16 µg/ml in PBS-0.05% Tween 20. Colour was developed by the addition of 100 µl TMB reagent (3',3',5',5',-tetramethylbenzidine plus $H_2O_2$), incubation at room temperature for 10 mins followed by the addition of 100 µl 1M Phosphoric acid and incubation at room temperature for 10 mins. Wells were then read at 450 nm in an ELISA micro plate reader. The results are shown in Table 2.

TABLE 2

| 1st addition | 2nd addition | 3rd addition | A450 |
|---|---|---|---|
| Periplasm | mouse anti FLAG ® | Goat anti-mouse Ig HRP | >3.000 (4 wells) |
| PBS | mouse anti FLAG ® | Goat anti-mouse Ig HRP | 0.124 ± 0.008 (3 wells) |
| PBS | PBS | Goat anti-mouse Ig HRP | 0.094 |

The positive result could arise from a combination of the binding of anti FLAG via the FLAG epitope, or the binding of the mouse IgG with the FB domain on the bifunctional molecule. Regardless of the proportional contributions from either of these reactions, the result demonstrates that the bifunctional molecule can be captured by anti human IgM capture antibodies.

Figure 9:
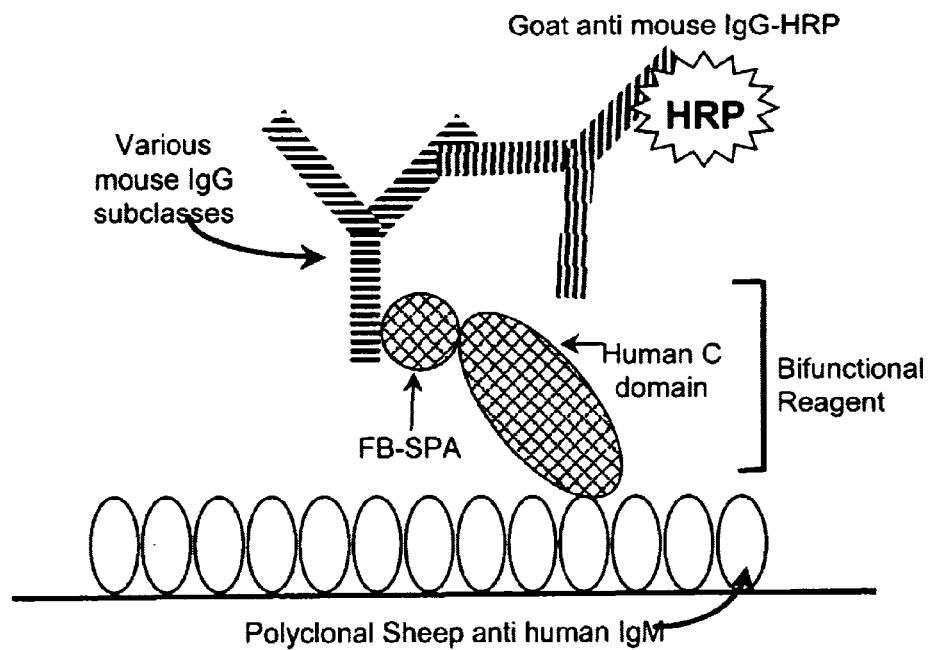

Property 2 was tested using an ELISA sandwich as shown in FIG. 9. Four mouse IgG subclasses were each individually tested for their ability to bind to the bifunctional molecule. Reagents were from AMIRAD, Melbourne, Australia (Mouse IgG1: 12CONT01 batch WD12A; IgG2a: 12CONT02 batch UI17A; IgG2b: 12HHLA01 batch UK18A; IgG3 Rota Ser4 batch UK07-B1). Each was diluted to 1 µg/ml with PBS/0.05% Tween20 before use. The control linker reagent FB-$C_H3\mu$ was diluted serially from 1/20 to 1/320 and 100 µl loaded into ELISA wells coated with stabilised sheep anti-human IgM (PanBio Pty Ltd) and incubated for 1 hour at 37° C. After 6 washes with PBS/0.05% Tween20 100 µl of each diluted mouse IgG subclass was added and the plate incubated a further hour at 37° C. After 6 washes in PBS/0.05% Tween20, 100 µl HRP-labelled goat anti mouse IgG Fc (Pierce Chemical Co. Rockford, Ill.) was added at 0.16 µg/ml. the plate then incubated for 1 hour and washed 6 times. The reaction was developed with 100 µl TMB solution for 10 min. stopped by adding 100 µl 1M phosphoric acid and the absorbance read at 450 nm. The results are shown in Table 3.

TABLE 3

| Dilution of Control linker reagent FBCH3µ | Mouse IgG1 1 µg/ml | Mouse IgG 2a 1 µg/ml | Mouse IgG 2b 1 µg/ml | Mouse IgG3 1 µg/ml |
|---|---|---|---|---|
| 1/20 | 2.425 | 1.134 | 0.762 | 0.599 |
| 1/40 | 2.007 | 0.555 | 0.787 | 0.489 |
| 1/80 | 2.010 | 0.776 | 0.578 | 0.289 |
| 1/160 | 1.429 | 0.581 | 0.399 | 0.373 |
| 1/320 | 1.123 | 0.320 | 0.309 | 0.302 |
| PBS | 0.260 (av of 3) | | | |

These results show that under the conditions of the reaction, the binding of mouse IgG subclasses to the control linker reagent is ranked in the following order: IgG1, IgG2a, IgG2b, IgG3, from highest to lowest. Control reagents formed using a *Staphylococcus* protein A fragment B-C domain linker would be most successful if mouse IgG1 is used to form the complex. It will be appreciated by those skilled in the art that if the subclass of the mouse monoclonal antibody is IgG3, a front end domain other than protein A would preferably be used to produce the bifunctional molecule. Suitable alternatives are described in the "Summary of the Invention" section of this specification.

The bifunctional molecule was separated from other periplasmic components by affinity chromatography on matrix bound mouse anti FLAG® antibody. The fraction which bound to the column was eluted with 0.1 M Glycine HCl pH 3.0 then adjusted to neutrality with saturated Tris. The bifunctional molecule (denoted FB-$C_H3\mu$) was concentrated to a final concentration of approx 1.2 mg/ml and used in an indirect ELISA test.

Human Herpes Virus 6 (HHV6) Indirect ELISA

Tissue culture supernatant containing mouse monoclonal antibody to HHV6 was diluted 1/50 PBS-0.05%Tween 20 and added to ELISA plates previously coated with HHV6 antigen and incubated at 37° C. for 30 min. After 4 washes with PBS-Tween, FB-$C_H3\mu$ was added to subsequent wells in doubling dilutions from 1/20 to 1/1280 in similar diluent and incubated a further 30 mins at 37° C. After 4 washes with diluent, polyclonal sheep anti human IgM labelled with horseradish peroxidase (AMRAD, Melbourne, 1/1500) was added and incubated 20 min at 37° C. Wells were washed 6 times with PBS and the peroxidase reaction was developed using 100 µl TMB solution (3',3',5',5'-Tetramethylbenizidine; BioChem ImmunoSystems Italia SPA) for 10 mins and the reaction stopped by the addition of 100 µl 1M Phosphoric acid. Results are presented in Table 4. The results demonstrate an effective positive reaction to dilutions as great as 1/80.

TABLE 4

| Dilution of FB-$C_H3$ µ | $A_{450}$ |
| --- | --- |
| No FB-$C_H3$ µ (zero) | 0.050 |
| 1/20 | 0.771 |
| 1/40 | 0.512 |
| 1/80 | 0.384 |
| 1/160 | 0.197 |
| 1/320 | 0.139 |
| 1/640 | 0.087 |
| 1/1280 | 0.079 |

Use of FB-$C_H3\mu$ control linker in AMRAD Hepatitis E antibody indirect ELISA

The control linker FB-$C_H3\mu$ was mixed with mouse IgG1 monoclonal antibody to the conformational epitope of Hepatitis E virus (Ref code 2E2) and used in an indirect ELISA test, comparing the response to positive and negative serum controls provided with the test kit (AMRAD, Melbourne, Vic). The control linker sample was partially purified and concentrated from material located in the periplasmic fraction. The control linker and mouse HEV antibody were mixed prior to the assay such that there was a dilution series of mouse monoclonal antibody from 0 to 50 µg/ml at control reagent dilutions of 1:10 and 1:50. The human positive control was serially diluted from 1/200 and the negative control diluted 1/200 with serum diluent supplied with the kit. Samples were added to an ELISA plate (AMRAD hepatitis E virus coated plates batch #1401H037) and incubated at room temperature for 30 min. After 3 washes with PBS/ 0.05% Tween20, 100 µl anti-human IgM-HRP conjugate (Silenus; 1:10,000) was added, incubated a further 30 min at room temperature, washed 3 times and TMB substrate added. After 10 min incubation, the reaction was stopped with 1M sulphuric acid and the plate read at 450 nm. The results are shown in Table 5.

TABLE 5

| 2E2 Mab | Control reagent Dilution | | Positive Control Dilution Series | |
| --- | --- | --- | --- | --- |
| conc (µg/ml) | 1:10 | 1:50 | Dilution | A450 |
| 50 | 2.92 | 1.828 | 1/200 | 2.745 |
| 25 | 2.931 | 1.795 | 1/400 | 2.135 |
| 10 | 2.880 | 1.772 | 1/800 | 1.525 |
| 5 | 2.900 | 1.703 | 1/1600 | 0.799 |
| 2 | 2.378 | 1.312 | 1/3200 | 0.505 |
| 1 | 2.112 | 0.792 | 1/6400 | 0.296 |
| 0 | 0.025 | 0.023 | 1/12800 | 0.168 |
| | | | Negative Control 1/200 | 0.103 |

These results show that Premixed FB-$C_H3\mu$ control linker/mouse monoclonal antibody can serve as a suitable positive IgM control in the AMRAD HEV ELISA assay. Levels which give comparable A450 to serum controls are:

Control Linker 1/10+Mab 2 µg/ml

Control Linker 1/50+Mab 50 µg/ml.

No significant background problems are observed indicating that this is a viable option to serum controls in the HEV assay.

EXAMPLE 5

Production of a bifunctional molecule containing the B fragment of *Staphylococcal* Protein A linked to a human IgG C-domain The gene sequences of human IgG constant domains 2 and 3 were separately amplified from cDNA prepared from mRNA isolated from human peripheral blood lymphocytes using polymerase chain reaction techniques. The design of the oligonucleotide primers used in the amplifications was based upon the 5' and 3' sequences for each of the heavy chain exons, obtained through Genbank accession no E06998.

Whereas *Staphylococcal* protein A (SPA) exhibits a stronger affinity for human IgG1, 2 and 4 than for mouse IgG subclasses, binding to human IgG3 is negligible (Reis et al, 1984). It has been suggested that the substitution of histidine with arginine at position 435 in IgG3 prevents the binding to Protein A (Deisenhofer, 1981). Therefore in order to minimise any self aggregation of a bifunctional construct between Fragment B of SPA and human IgG C domains, it would be preferable to have any C3γ domain sequence contain the IgG3 mutation, $Arg^{435}$. It is not possible to selectively amplify IgG3 constant region sequences from cDNA because of the close homology of the 5' and 3' terminal sequences between all human IgG subclasses. Consequently the mutation was performed subsequent to the amplification and cloning using the QuikChange™ Site Directed mutagenesis kit (Stratagene, La Jolla, Calif.).

Sequences coding for NotI and SacII sites were added to the 5' and 3' end respectively of $C_H2\gamma$ and $C_H3\gamma$ sequences to enable insertion into the expression vector pGC FB-$C_H3\mu$ shown in FIG. 8, from which the $C_H3\mu$ sequence was removed as a NotI-SacII fragment.

Expression in *E. coli* and purification of product was performed as described in Example 4.

PanBio IgG Indirect Dengue ELISA using FB-$C_H2\gamma$ and FB-$C_H3\gamma$ control linkers Test samples were unfractionated periplasmic fractions containing FB-$C_H2\gamma$ and FB-$C_H3\gamma$ control linkers from 500 ml expression cultures. Samples were used neat or diluted 1:10 in PBS/0.05% Tween 20.

Mouse anti dengue monoclonal antibody was clone 13C11 (IgG2a) obtained from PanBio Ltd (Windsor, Qld) at 1.6 mg/ml and used at a final concentration of 1.6 µg/ml diluted in PBS/0.05% Tween 20.

The human positive serum control containing anti dengue IgG antibodies was obtained from PanBio Ltd and is identical to what is supplied in their commercial dengue ELISA test. It was used at a dilution of 1:100 in PBS/0.05% Tween 20.

HRP-labelled sheep anti human IgG (lot TJ19B) was from Silenus/AMRAD (Melbourne) and used at a dilution of 1:1000 in PBS/0.05% Tween 20.

The ELISA plate coated with dengue antigens was as supplied by PanBio in their commercial Dengue ELISA test. It was used without further blocking. All incubations were for 1 hour at 37° C. followed by 3×2 min washes with PBS/0.05% Tween 20.

The first layer of the ELISA contained 100 µl 13C11 mouse anti dengue monoclonal antibody; control wells contained PBS/0.05% Tween 20. Following incubation and washing as described the samples containing FB-$C_H2\gamma$ and FB-$C_H3\gamma$ were added. Controls contained either human anti dengue IgG serum 1:100 or PBS/0.05% Tween 20. Following incubation and washing, HRP-labelled sheep anti human IgG 1:1000 was added. After incubation and washing, 100 µl TMB solution (containing $H_2O_2$) was added and incubated for 10 min at room temperature to develop the colour reaction. 100 µl 1M phosphoric acid was added to stop the reaction and the plate read in a micro plate reader at 450 nm. Results are shown in Table 6.

TABLE 6

|  | A450 | |
|---|---|---|
| 13C11mAb + FB-$C_H3\gamma$ periplasm | 1.475 | 1.220 |
| PBS-Tween + FB-$C_H3\gamma$ periplasm (control) | 0.564 | |
| 13C11mAb + FB-$C_H3\gamma$ periplasm 1:10 | 0.901 | 0.825 |
| PBS-Tween + FB-$C_H3\gamma$ periplasm 1:10 (control) | 0.268 | |
| 13C11mAb + FB-$C_H2\gamma$ periplasm | 0.856 | 0.814 |
| PBS-Tween + FB-$C_H2\gamma$ periplasm (control) | 0.411 | |
| 13C11mAb + FB-$C_H2\gamma$ periplasm 1:10 | 0.545 | 0.521 |
| PBS-Tween + FB-$C_H2\gamma$ periplasm 1:10 (control) | 0.279 | |
| PBS-Tween + human anti dengue IgG positive control 1:100 | 0.930 | 0.922 |
| PBS-Tween + PBS-Tween | 0.276 | 0.265 |

Both periplasmic fractions containing FB-$C_H2\gamma$ and FB-$C_H3\gamma$ provide positive reactions in this ELISA when linked with the mouse anti dengue mAb, 13C11, compared to controls. The linker containing the $C_H3\gamma$ domain is the preferred construct to mix with a specific mouse monoclonal antibody to use as a replacement IgG positive control reagent.

EXAMPLE 6

Bifunctional construct using core streptavidin as the Ig binding domain

The protein streptavidin produced by *Streptomyces sp.* has an affinity ($K_D$) for biotin of the order of $10^{-15}$ M (Green, 1975; Pähler et al., 1987) Commercially produced streptavidin consists of a N- and C- terminally shortened form, called core streptavidin (Argaraña et al., 1986) comprising the sequence from Ala[13] or Glu[14] to Ala[138] to Ser[139] of the mature polypeptide. Core streptavidin is more soluble than the full length protein and its binding activity for biotinylated proteins is significantly enhanced (Bayer et al., 1989).

The nucleotide sequence for the intact streptavidin gene from *Streptomyces avidinii* was obtained from Genbank accession no. X03591 (Argaraña et al., 1986).

The structural gene encoding core streptavidin was amplified from chromosomal DNA of *S. avidinii* (ATCC27419) using Pfu DNA polymerase and oligonucleotides able to recognise the 5' and 3' sequences of the core streptavidin (codons from Ala[13] to Ser[139]). The oligonucleotide primers also contained sequences flanking the 5' and 3' streptavidin sequences for restriction sites (in particular NcoI at the 5' end and NotI at the 3' end to enable the core streptavidin gene to be inserted into the vector pGC (Coia et al., 1996) which already contains the sequence for the human IgM $C_H3$ domain, in the configuration streptavidin-C domain. The sequence coding for the FLAG5® tag epitope (Hopp et al., 1998) lies 3' to the C domain to enable the FLAG® tag to be expressed as a C-terminal peptide on the molecule.

The amplified core streptavidin gene was inserted into the PCR-Script™ SK(+) plasmid using the PCR-Script™ Cloning Kit obtained from Stratagene, La Jolla, Calif. (Cat no. 211190-5). After the DNA sequence was confirmed in positive transformants, the core streptavidin sequence was excised from the plasmid by double digestion with NcoI and NotI, and ligated into a likewise digested pGC vector containing the DNA sequence for human IgM $C_H3$ domain.

The verified sequence of the expression cassette in pGC comprising the pel B leader sequence, core streptavidin, human IgM $C_H3$ domain and FLAG® tag is shown in SEQ ID NO: 4 and FIG. 10.

Expression in *E. coli* was performed as described in Example 4. Cells from a 500 ml culture were fractionated into periplasmic fraction, cytoplasmic and membrane fraction. The periplasmic fraction was prepared using the protocol of Minsky et al. (1986). The cell pellet remaining after centrifugation to obtain the periplasmic supernatant was resuspended in TE buffer (10mM Tris HCl pH 7.4, 1mM EDTA) sonicated and centrifuged at 20,000xg to obtain the soluble cytoplasmic fraction and the membrane pellet. Western blot analysis of each of the three fractions using the FLAG® tag as a probe indicated that while the expressed product was present in all three fractions, the membrane pellet contained the highest levels.

Figure 11:
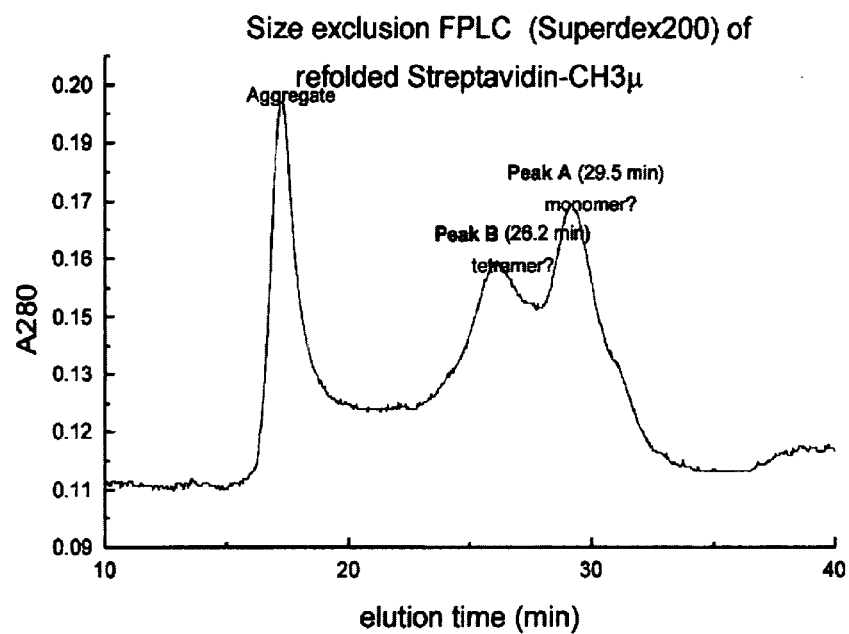

The membrane fraction was dissolved in 10 ml 6M guanidinium HCl, pH 1.5 (Schmidt and Skerra, 1994), dialysed twice against 200 ml 6M guanidinium HCl, pH 1.5, then twice against 2 L PBS at 4° C. After centrifugation to remove insoluble aggregate, the supernatant was fractionated on a Superdex 200 (HR 10/30, Pharmacia LKB Biotechnology) column run in PBS at 0.5 ml/min. The elution profile is shown in FIG. 11. All three peaks probed with FLAG® indicating the presence of the product. The first peak is high molecular weight aggregate eluting at the void volume of the column. The second and third peaks were collected separately and labelled preparation B (0.10 mg/ml) and preparation A (0.17 mg/ml) respectively. Both preparations showed bands on Western blot of identical size, and so the size difference between the two preparations is related to the multimerisation state of the product. Both preparations were used in tests as described below.

Use of Control Reagent Streptavidin-$C_H3\mu$ in PanBio Dengue Indirect ELISA

In this test, a complex is formed between biotinylated monoclonal mouse IgG to dengue antigens (13C11-B) and streptavidin linked to human IgM $C_H3$ domain (strep-$C_H3\mu$) to mimic positive human IgM antibody to dengue, and used as a pseudo positive control in commercial IgM capture Dengue ELISA and indirect IgM Dengue ELISA kits where the response is compared to positive and negative controls provided in the kit.

Biotinylation of mouse monoclonal anti dengue IgG (Clone 13C11)

2.56 mg of 13C11 Monoclonal antibody (IgG fraction) to dengue antigen (PanBio Ltd, Windsor, Qld; product 13C7001) was equilibrated in 1 ml 50mM sodium bicarbonate buffer, pH 8.0. To this was added 75 μl freshly prepared EZ-Link™ Sulfo-NHS-LC-Biotin solution (1 mg/ml in water) (Pierce Chemical Company, Rockford, Ill.; product code 21335), and incubated at room temperature for 1 hour. After the sample had undergone extensive dialysis against PBS (phosphate buffered saline, final sample volume 1.2 ml), the protein concentration was estimated by absorbance at 280 nm to be 1.6 mg/ml.

The success of the biotinylation reaction was confirmed by ELISA, in which dilutions of the biotinylated 13C11 antibody was added to wells containing immobilised dengue antigen. Non biotinylated 13C11 was used as a negative control. A streptavidin-horse radish peroxidase conjugate was used to visualise the presence of the biotinylated 13C11 antibody.

Dengue IgM Indirect ELISA

The reagents used in this assay were as follows:

ELISA plate coated with dengue 2 antigen (PanBio Pty Ltd, Windsor Qld)

IgM Positive Control Serum, IgM Cut-off Calibrator Serum. Negative Control Serum for IgM (PanBio Pty Ltd provided in the kit)

Biotinylated mouse anti dengue IgG (clone 13C11), concentration=1.6 mg/ml (biotinylation was performed as described above).

Non biotinylated mouse anti dengue IgG (clone 13C11), concentration=1.6 mg/ml

Control Linker Reagent: Strep-$C_H3\mu$ Preparation A, concentration 0.17 mg/ml.

Control linker reagent was mixed with biotinylated and non-biotinylated 13C11 Mab prior to the assay in the following proportions:

1. 13C11-Biotin (1/10,000)+Control Linker Prep A 1/10
2. 13C11-Biotin (1/10,000)+Control Linker Prep A 1/100
3. 13C11-Biotin (1/10,000)+Control Linker Prep A 1/1000
4. 13C11 (1/10,000) [nonbiotinylated]+Control Linker Prep A 1/10
5. 13C11 (1/10,000) [nonbiotinylated]+Control Linker Prep A 1/100
6. 13C11 (1/10,000) [nonbiotinylated]+Control Linker Prep A 1/1000

Dilution was in serum diluent (Tris buffered saline with preservatives and additives) as supplied in the kit. Mixing took place at room temperature for 10 min with rotation.

Additions to ELISA plate were in the following order:

1. Samples as above, blank, positive, negative and cut-off serum controls (100 μl) incubated at 37° C. for 1 hour, followed by 6 washes with diluted wash buffer.

2. HRP-labelled sheep anti Human IgM (Silenus/AMRAD; Code MAH) 100 μl of 1/1000 dilution; incubated for 1 hour at 37° C. followed by 6 washes with diluted wash buffer.

3. Reaction was developed with 100 μl TMB reagent 10 min at room temperature, followed by the addition of 100 μl 1M phosphoric acid. Samples were read at 450 nm.

The results obtained from this indirect assay are shown in Table 7.

TABLE 7

| Sample | A450 |
|---|---|
| Blank (Serum diluent only) | 0.058 |
| Negative serum Control 1/100 | 0.063 |
| Positive Serum Control 1/100 | 1.419 |
| Positive Cut-Off 1/100 | 0.522 |
| Positive Cut-Off 1/100 (duplicate) | 0.580 |
| Control Linker 1/10 + 13C11-biotin | 1.186 |
| Control Linker 1/10 + 13C11-biotin (dup) | 1.109 |
| Control Linker 1/100 + 13C11-biotin | 1.070 |
| Control Linker 1/100 + 13C11-biotin (dup) | 1.076 |
| Control Linker 1/1000 + 13C11-biotin | 0.212 |
| Control Linker 1/1000 + 13C11-biotin (dup) | 0.183 |
| Control Linker 1/10 + 13C11 | 0.151 |
| Control Linker 1/100 + 13C11 | 0.059 |
| Control Linker 1/1000 + 13C11 | 0.074 |

These results show tha the complex formed between the Strep-$C_H3\mu$ linker reagent and the biotinylated mouse anti dengue IgG (13C11) acted as a human positive control up to a dilution of at least 1/100. No reaction was observed if the mouse monoclonal IgG was not biotinylated, or if there was insufficient control linker reagent to capture the biotinylated mouse Mab.

Use of Control Reagent Streptavidin-$C_H3\mu$ in PanBio Dengue IgM Capture ELISA The Dengue IgM capture ELISA test kit from PanBio Ltd (Windsor, Qld; Cat No DEMF-200) was used for this demonstration. The positive and cut-off control sera provided contain human IgM antibodies to dengue. The negative control serum contains human IgM antibodies, but with no specificity for dengue antigens.

Two test samples of the Streptavidin-Human $C_H3$ μ domain linker reagent were used:

a) Preparation A, 0.17 mg/ml b) Preparation B, 0.10 mg/ml

These preparations were mixed with biotinylated and non-biotinylated 13C11 Mab as described below.

The following samples were prepared for ELISA:

1. Blank—100 μl serum diluent only, provided in PanBio kit

2. Negative Control Serum—from PanBio kit; 100 μl, diluted 1/100 in serum diluent.

3. IgM Positive Control Serum—from PanBio kit; 100 μl, diluted 1/100 in serum diluent.

4. Cut-off Calibrator—from PanBio kit; 100 μl, diluted 1/100 in serum diluent.

5. Strep-$C_H3\mu$ Preparation A+13C11-Biotin: 10 μl of prepA diluted to 1 ml with serum diluent to which 1 μl 13C11-Biotin (1/1000 dilution) was added (Final concentration of PrepA protein=1.7 μg/ml; 13C11-Biotin=1.6 μg/ml).

6. Strep-$C_H3\mu$ Preparation B+13C11-Biotin: 10 μl of prepB diluted to 1 ml with serum diluent to which 1 μl 13C11-Biotin (1/1000 dilution) was added (Final concentration of PrepB protein=1.0 μg/ml; 13C11-Biotin=1.6 μg/ml).

7. Blank+13C11-Biotin (negative control) 1 μl 13C11-Biotin was added to 1 ml serum diluent (Final concentration of 13C11 biotin=1.6 μg/ml).

8. Strep-$C_H3\mu$ Preparation A+13C11 (non biotinylated) (negative control): 10 μl of prepA diluted to 1 ml with serum diluent to which 1 µl 13C11 (1/1000 dilution) was added (Final concentration of PrepA protein=1.7 µg/ml; 13C11=1.6 µg/ml).

9. Strep-$C_H3\mu$ Preparation B+13C11 (non biotinylated) (negative control): 10 µl of prepB diluted to 1 ml with serum diluent to which 1 µl 13C11 (1/1000 dilution) was added (Final concentration of PrepB protein=1.0 µg/ml; 13C11=1.6 µg/ml).

10. Blank+13C11 (negative control) 1 µl 13C11-Biotin was added to 1 ml serum diluent (Final concentration of 13C11 biotin=1.6 µg/ml).

Each sample was mixed on a rotating wheel for 10 min at room temperature, then 100 µl of each (some in duplicate) were added to ELISA strips from the test kit which were pre-coated with polyclonal sheep anti human IgM. The strips were covered and incubated at 37° C. for 60 min, then washed three times for 2 min with PBS containing 0.05% Tween 20. At the same time as the above incubation, 2 ml conjugated monoclonal antibody tracer (PanBio: anti dengue-HRP) was added to one vial of lyophilised dengue antigen (serogroups 1–4) and rocked gently at room temperature to aid in the dissolution of the dengue antigen. After the above washes, 100 µl of the HRP conjugate was added to each well, incubated for 60 min at 37° C. then washed three times for 2 min with PBS-0.05% Tween 20. 100 µl of TMB reagent (3',3',5',5' tetramethylbenzidine/hydrogen peroxide; supplied with the kit) was then added to each well and the strips incubated at room temperature for 10 mins. The reaction was stopped by the addition of 100 µl 1M phosphoric acid and the colour intensity read at 450 nm. Results of this assay are shown in Table 8.

TABLE 8

| Sample | A450 |
|---|---|
| Blank (serum diluent only) | 0.115 |
| Negative serum control | 0.121 |
| IgM positive serum control | 2.678 |
| Positive Cut-off Calibrator | 1.198 |
| Positive Cut-off Calibrator (duplicate) | 1.235 |
| Preparation A + 13C11-biotin | 1.914 |
| Preparation A + 13C11-biotin (duplicate) | 1.850 |
| Preparation B + 13C11-biotin | 1.200 |
| Preparation B + 13C11-biotin (duplicate) | 1.344 |
| Blank + 13C11-biotin | 0.115 |
| Blank + 13C11-biotin (duplicate) | 0.128 |
| Preparation A + 13C11(non biotinylated) | 0.142 |
| Preparation A + 13C11(non biotinylated) | 0.126 |
| Preparation B + 13C11(non biotinylated) | 0.113 |
| Preparation B + 13C11(non biotinylated) | 0.124 |
| Blank + 13C11(non biotinylated) | 0.106 |

Both preparations of Strep-$C_H3\mu$ gave positive reactions in the ELISA at levels sufficient for the complex with mouse IgG to be used as a replacement for the positive control serum. The lower reading with preparation B can be partly attributed to the lower concentration of the product. Results with the controls indicated that there were no significant background problems.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Åkerstrom, B. and Björck, L (1989) Protein L: an immunoglobulin light chain-binding bacterial protein. Characterization of binding and physicochemical properties. J. Biol. Chem. 264: 19740–19746.

Argaraña, C. E., Kuntz, I. D., Birken, S., Axel, R. and Cantor, C. R. Molecular cloning and nucleotide sequence of the streptavidin gene. Nucl. Acids Res. 14 1871–1882.

Bayer, E. A., Ben-Hur, H., Hiller, Y., and Wilchek, M. (1989) Post-secretory modifications of streptavidin. Biochem. J. 259 369–376.

Better, M., Chang, C. P., Robinson, R. R., and Horwitz, A. H. (1988) Escherichia coli secretion of an active chimeric antibody fragment. Science 240, 1041–1043.

Björck, L. and Kronvall, G. (1984) Purification and some proerties of streptococcal protein G, a novel IgG-binding reagent. J. Immunol. 133, 969–974.

Borza, D-B., Tatum, F. M. and Morgan, W. T. (1996) Domain Structure and Conformation of Histidine-Proline-Rich Glycoprotein. Biochemistry 35 1925–1934.

Boulianne, G. L., Hozumi, N. and Shulman, M. J. (1984) Production of functional chimaeric mouse/human antibody. Nature (Lond.) 312, 643–646.

Boyle, M. D. P. and Reis, K. J. (1987) Bacterial Fc receptors. Bio/technology 5, 697–703.

Coia G., Hudson, P. J. and Lilley G. G. (1996) Construction of recombinant extended single-chain antibody peptide conjugates for use in the diagnosis of HIV1 and HIV2. J. Immunol. Methods. 192, 13–23.

Diesenhofer, J., (1981). Crystallographic refinement and atomic models of a human Fc fragment and its complex with fragment B of protein A from Staphylococcus aureus at 2.9- and 2.8 Å resolution. Biochemistry 20, 2361–2370.

Dolezal, O., Coia, G., Guthrie, R. E., Lilley, G. G. and Hudson, P. J. (1995) Escherichia coli expression of a bifunctional Fab-peptide epitope reagent for the rapid diagnosis of HIV-1 and HIV-2 Immunotechnology 1 197–209.

Dorai, H. and Gillies, S. D. (1989) The complete nucleotide sequence of a human immunoglogulin genomic C µ gene. Nucleic Acids Research 17, 6412

Gorgani, N. N., Parish, C. R., Easterbrook Smith, S. B., and Altin, J. G. (1997) Histidine-Rich Glycoprotein binds to Human IgG and C1$q$ and inhibits the formation of insoluble immune complexes. Biochemistry 36 6653–6662.

Green, N. M. (1990) Avidin and Streptavidin. Methods in Enzymol. 184 51–67.

Hamilton. R. G. (1990) Engineered human antibodies as immunologic quality control reagents. Ann. Biol. Clin. 48, 473–477.

Hamilton R. G. (1991) Application of engineered chimeric antibodies to the calibration of human antibody standards. Ann. Biol. Clin. 49, 242–248.

Heusser C. H., Anderson, C. L. and Grey, H. M. (1977) Receptors for IgG: subclass specificity of receptors on different mouse cell types and the definition of two distinct receptors on a macrophage cell line. J. Exp. Med 145, 1316–1327.

Hogarth, P. M., Hibbs, M. L., Bonadonna, L., Scott, B. M., Witort, E. Pieterz, G. A. and McKenzie, I. F. (1987) Immunogenetics 26, 161–168.

Hopp, T. P., Prickett, K. S., Price, V. L., Libby, R. T., March C. J., Cerretti, D. P., Urdal, D. L. and Conlon, P. J. (1988). A short polypeptide marker sequence useful for recombinant protein identification and purification. Bio/Technology 6, 1204–1210.

Huston, J. S., Mudgett-Hunter, M., Tai, M.-S., McCartney, J. E., Warren, F. D., Haber, E., and Oppermann, H (1991) Protein engineering of single chain Fv analogs and fusion proteins. Methods Enzymol. 203, 46–88.

Kulcczycki, A. Jr., Webber, J., Soares, H. A., Onken, M. D., Thompson, J. A., Chaplin, D. D., Loh, D. Y. and Tillinghast J. P. (1990) Genomic organization of mouse Fc receptor genes. Proc. Natl. Acad. Sci. USA 87, 2856–2960.

Minsky, A., Summers, R. G. and Knowles, J. R. (1986) Secretion of beta lactamase into the periplasm of Escherichia coli: Evidence for a distinct release step associted with a conformational change. Proc. Nat.l Acad. Sci. USA 83 4180–4184.

Morrison, S. L., Johnson, M. J. Herzenberg, L. A. and Oi, V. T. (1984) Chimeric human antibodies: mouse antigen binding domains with human constant regions. Proc Natl. Acad. Sci. USA 81, 6851–6855.

Pähler, A., Henderickson, W. A., Kolks, M. A., Aragaña, C. E., and Cantor C. R. Characterization and crystallization of core streptavidin J. Biol. Chem. 262 13933–13937.

Reichmann, L., Clark, M., Waldmann, H. and Winter G. (1998) Reshaping human antibodies for therapy. Nature (Lond.) 332, 323–327.

Reis, K. J., Ayoub, E. M., and Boyle, M. D. P. (1984) Streptococcal Fc Receptors II Comparsion of the reactivity of a receptor from a group C Streptococcus with staphylococcal protein A. J. Immunol. 132, 3098–3102.

Rylatt, D. B., Kemp, B. E., Bundesen, P. G., John, M. A., O'Reilly, E. J., Coittis, L. E., Miles, S. J., Khan, J. M., Dinh, D. P., Stapleton, D. and Hillyard, C. J. (1990). A rapid whole-blood immunoassay system. Med. L. Aust. 152, 75–77.

Sang, C. T., Cuzzubbo, A. J. and Devine, P. L. (1998) Evaluation of commerical capture Enzyme-Linked Immunosorbent Assay for the determination of IgM and IgG antibodies produced during dengue infection. Clinical Diagnotic Laboratory Immunology 5, (1) in press.

Schmidt, T. G. M. and Skerra, A. (1994) One-step affinity purification of bacterially produced proteins by means of the "Strep tag" and immobilized recombinant core streptavidin. J Chromatog. A 676, 337–345.

Segal, D. M. and Titus, J. A. (1978) The subclass specifically for the binding of murine myeloma proteins to macrophages and lymphocyte cell lines and to normal spleen cells J. Immunol. 120, 1395–1403.

Skeera A. (1993) Bacterial expression of immunoglobulin fragments. Curr. Opin. Immunol. 5, 256–262.

Uhlen, M., Guss, B., Nilsson, B., Gatenvack, S., Philipson, L. and Lindberg, M. (1984) Complete sequence of the Staphylococcal gene encoding Protein A. J. Biol. Chem. 259, 1695–1702.

Unkeless, J. C., Scigliano, E. and Freedman, V. H. (1988) Structure and function of human and murine receptors for IgG (1988) Ann. Rev. Immunol 6, 251–281.

Winter, G. and Milstein, C. (1991) Man-made antibodies. Nature (Lond.) 349, 293–299.

Yanisch-Perron, C., Vieira, J., and Messing, J. (1985) Improved M13 phage cloning vectors and host strains: nucleotide sequences of the M13mp18 and pUC 19 vectors. Gene 33, 103–119.

Zhou, H., Fisher, R. J. and Papas, T. S. (1994) Optimization of primer sequences for mouse repertoire display library construction. Nucleic Acids Research 22, 888–889.

What is claimed is:

1. A complex formed between (i) an antibody or biologically active fragment thereof from a first species and (ii) a bifunctional molecule, the bifunctional molecule comprising a binding region of non-antibody origin which binds to the antibody of the first species and a constant region from an antibody of a second species, the constant region comprising at least one $C_H$ domain or an epitoge thereof, wherein the bifunctional molecule is bound to the constant region of the antibody of the first species, wherein the binding region comprises a protein selected from the group consisting of a mouse Fc γ receptor, histidine rich glycoprotein, *Streptococcal* protein G, *Staphylococcal aureus* protein A, *Peptostreptococcus magnus* protein L, and antibody-binding fragments thereof.

2. The complex according to claim 1, in which the binding region comprises fragment B of *Staphylococcus aureus* protein A.

3. The complex according to claim 1, in which the binding region comprises a mouse Fc γ receptor or fragment thereof.

4. The complex according to claim 1, in which the binding region comprises histidine rich glycoprotein.

5. A complex formed between (i) an antibody or biologically active fragment thereof from a first species and (ii) a bifunctional molecule, the bifunctional molecule comprising a binding region of non-antibody origin which binds to one or more non-naturally occurring groups provided on the antibody of the first species, and a constant region from an antibody of a second species, the constant region comprising at least one $C_H$ domain or an epitope thereof, wherein the bifunctional molecule is bound to one or more non-naturally occurring groups provided on the constant region of the antibody of the first species, wherein the non-naturally occurring group is a biotin molecule and the binding region comprises streptavidin or a fragment thereof.

6. The complex according to claim 1 or 5, wherein the binding region has a $K_D$ for the antibody of the first species of less than $10^{-6}$ M.

7. The complex according to claim 6 in which the binding region has a $K_D$ for the antibody of the first species of less than $10^{-8}$ M.

8. The complex according to claim 1 or 5, wherein the constant region from the antibody of the second species comprises one or more constant domains from an IgM antibody.

9. The complex according to claim 8, in which the constant region from the antibody of the second species comprises one or more $C_H3\mu$ domains.

10. The complex according to claim 1 or 5, wherein the constant region from the antibody of the second species comprises one or more constant domains from an IgG antibody.

11. The complex according to claim 10, in which the constant region from the antibody of the second species comprises one or more $C_H3\gamma$ domains.

12. The complex according to claim 1 or 5, wherein the constant region from the antibody of the second species comprises one or more constant domains from an IgA antibody.

13. The complex according to claim 1 or 5, wherein the constant region from the antibody of the second species comprises or consists of a non-naturally occurring combination of immunoglobulin $C_H$ domains or epitopes thereof.

14. The complex according to claim 1 or 5, in which the antibody constant region consists of a single $C_H$ domain.

15. The complex according to claim 1 or 5, in which the first species is a rat or mouse.

16. The complex according to claim 1 or 5, wherein the second species is a human.

17. The complex according to claim 1 or 5, wherein the binding region and the constant region from the antibody of the second species are linked directly or are separated by a linker molecule of between 1 and 20 amino acids in length.

* * * * *